(12) United States Patent
Black et al.

(10) Patent No.: US 10,660,535 B2
(45) Date of Patent: May 26, 2020

(54) DIRECTIONAL-SPECIFIC EXTRANEURAL RECORDING DEVICE

(71) Applicants: Iian Black, Boca Raton, FL (US); James Abbas, Scottsdale, AZ (US); Ranu Jung, Coral Gables, FL (US)

(72) Inventors: Iian Black, Boca Raton, FL (US); James Abbas, Scottsdale, AZ (US); Ranu Jung, Coral Gables, FL (US)

(73) Assignee: The Florida International University Board of Trustees, Miami, FL (US)

( * ) Notice: Subject to any disclaimer, the term of this patent is extended or adjusted under 35 U.S.C. 154(b) by 332 days.

(21) Appl. No.: 15/634,967

(22) Filed: Jun. 27, 2017

(65) Prior Publication Data

US 2018/0368711 A1 Dec. 27, 2018

(51) Int. Cl.
  *A61B 5/04* (2006.01)
  *A61B 5/00* (2006.01)

(52) U.S. Cl.
  CPC ........ *A61B 5/04001* (2013.01); *A61B 5/6877* (2013.01); *A61B 5/4836* (2013.01); *A61B 2560/0475* (2013.01); *A61B 2562/0215* (2017.08); *A61B 2562/043* (2013.01); *A61B 2562/164* (2013.01)

(58) Field of Classification Search
  CPC . A61B 5/04001; A61B 5/4041; A61B 5/4047; A61B 5/4052; A61B 5/6877; A61B 5/4836; A61B 2562/0215; A61B 2562/0475; A61B 2562/043; A61B 2562/164
  See application file for complete search history.

(56) References Cited

U.S. PATENT DOCUMENTS

| 4,602,624 A | * | 7/1986 | Naples | A61N 1/0556 607/118 |
| 2011/0021943 A1 | * | 1/2011 | Lacour | A61N 1/0551 600/546 |
| 2017/0311827 A1 | * | 11/2017 | Choi | A61F 2/72 |

OTHER PUBLICATIONS

Parisa Sabetian, Milos R. Popvic, Paul B. Yoo, "Directionally-Sensitive Peripheral Nerve Recording: Bipolar Nerve Cuff Design", 2016, 38th Annual International Conference of the IEEE Engineering in Medicine and Biology Society (Year: 2016).*
Fitzgerald et al., "Microchannels as axonal amplifiers," IEEE Transactions on Biomedical Engineering, Mar. 2008, pp. 1136-1145, vol. 55, No. 3.
Stein et al., "Predicted amplitude and form of action potentials recorded from unmyelinated nerve fibres," Journal of Theoretical Biology, Sep. 1971, pp. 539-558, vol. 32.
Stein et al., "Stable long-term recordings from cat peripheral nerves," Brain Research, Jun. 1977, pp. 21-38, vol. 128.
(Continued)

*Primary Examiner* — Eun Hwa Kim
*Assistant Examiner* — Adam Z Minchella
(74) *Attorney, Agent, or Firm* — Saliwanchik, Lloyd & Eisenschenk

(57) ABSTRACT

Devices, systems, and methods for recording action potential (AP) from a nerve are provided. A device can include a cuff or a microchannel to be used to record an AP from a nerve. A recording electrode can be included within a channel of the cuff or microchannel, and the recording electrode can be offset or off-center such that it is not located mid-channel within the recording cuff or microchannel.

20 Claims, 19 Drawing Sheets

(56) References Cited

OTHER PUBLICATIONS

Struijk et al., "Cuff electrodes for long-term recording of natural sensory information," IEEE Engineering in Medicine and Biology, May/Jun. 1999, pp. 91-98.

Brindley, "An implant to empty the bladder or close the urethra," Journal of Neurology, Neurosurgery, and Psychiatry, Apr. 1977, pp. 358-369, vol. 40.

Chew et al., "A microchannel neuroprosthesis for bladder control after spinal cord injury in rat," Science Translational Medicine, Nov. 6, 2013, pp. 1-10, vol. 5, No. 210.

Hoffer et al., "Flow to use nerve cuffs to stimulate, record or modulate neural activity," Neural Prostheses for Restoration of Sensory and Motor Function, 2001, pp. 1-26.

Marks et al., "Action currents, internodal potentials, and extracellular records of myelinated mammalian nerve fibers derived from node potentials," Biophysical Journal, Jun. 1976, pp. 655-668, vol. 16.

Meier et al., "Extracellular potentials from active myelinated fibers inside insulated and noninsulated peripheral nerve," IEEE Transactions on Biomedical Engineering, Sep. 1998, pp. 1146-1153, vol. 45, No. 9.

Paintal, "The influence of diameter of medullated nerve fibres of cats on the rising and falling phases of the spike and its recovery," The Journal of Physiology, Jun. 1966, pp. 791-811, vol. 184.

Pearson et al., "Properties of action potentials from insect motor nerve fibres," Journal of Experimental Biology, Apr. 1970, pp. 299-316, vol. 53.

Stein et al., "Principles underlying new methods for chronic neural recording," The Canadian Journal of Neurological Sciences, Aug. 1975, pp. 235-244.

Struijk, "The extracellular potential of a myelinated nerve fiber in an unbounded medium and in nerve cuff models," Biophysical Journal, Jun. 1997, pp. 2457-2469, vol. 72.

Struijk et al., "Tripolar nerve cuff recording: stimulus artifact, EMG, and the recorded nerve signal," Proceedings of the 17th International Conference of the Engineering in Medicine and Biology Society, Sep. 1995, pp. 1105-1106.

* cited by examiner

DIRECTIONAL-SPECIFIC EXTRANEURAL RECORDING DEVICE

BACKGROUND

Extraneural electrodes are the only class of peripheral nerve interface to be chronically implanted in humans to address functional deficits due to neurological impairment. Chronically implanted cuff electrodes have been used to stimulate motor nerves that innervate the lower- and upper-limb musculature to correct excessive foot drop in individuals following stroke and to produce functional movements such as hand grasping and standing in individuals with spinal cord injury (Hoffer & Kallesoe, 2001). Stimulation of ventral sacral roots in humans using cuff electrodes have been implanted in thousands of paralyzed people to restore the volitional control of bladder and bowel function as well as sexual function (Brindley, 1977). Microchannel electrode arrays developed recently have shown promise as a tool to incorporate sensory feedback of bladder fullness into a closed-loop bladder control system (Chew et al., 2013).

The early success of cuff electrodes as long-term interfaces for recording neural activity in peripheral nerves (Brindley, 1977; Hoffer & Kallesoe, 2001; R. B. Stein et al., 1975; R. B. Stein, Nichols, Jhamandas, Davis, & Charles, 1977) motivated the development of early mathematical models to better understand the relationship between action potentials, channel configuration, and the signals one could expect to record (Marks & Loeb, 1976; R. Stein & Pearson, 1971). These models were developed under two critical assumptions, namely that 1) radial currents, perpendicular to the long axis of the channel, are zero, and 2) the extracellular potentials at both ends of the channel are always zero. Modeling studies use a recording electrode fixed at mid-channel to explore the dependency of extracellular potentials on other parameters, such as action potential shape and conduction velocity, proximity of nodes of Ranvier to the recording electrode, and cuff length and diameter (Marks & Loeb, 1976; R. Stein & Pearson, 1971; Johannes Jan Struijk, 1997).

BRIEF SUMMARY

Embodiments of the subject invention provide devices, systems, and methods for recording action potential (AP) from a nerve. A device can include, for example, a cuff or a microchannel to be used to record an AP from a nerve (e.g., a nerve of a subject such as a mammalian subject (e.g., a human subject)). An electrode can be included (e.g., within a channel or lumen or channel lumen of the cuff or microchannel), and the (recording) electrode can be offset or off-center (i.e., not located mid-channel within the recording cuff or microchannel). Related art recording devices position the electrode mid-channel (centered) within the cuff or microchannel.

In an embodiment, a device for recording neural activity can comprise a substrate (e.g., a cuff or a microchannel) to be positioned on a nerve and comprising a channel formed therewithin, and a first recording electrode disposed within the channel for recording neural activity of the nerve. The first recording electrode can be positioned in an offset position with respect to a length of the channel, such that the first recording electrode is located closer to a first end of the channel than it is to a second end of the channel opposite from the first end. The recording device can further include a second recording electrode positioned in an offset position with respect to the length of the channel (and on the other side of the midpoint of the channel from the first recording electrode), such that the second recording electrode is located closer to the second end of the channel than it is to the first end of the channel.

BRIEF DESCRIPTION OF DRAWINGS

FIG. 15A is for an M&L waveform; FIG. 15B is for a P&B waveform; FIG. 15C is for a triangularized representation of the M&L waveform of FIG. 15A; and FIG. 15D is for a triangularized representation of the P&B waveform of FIG. 15B. For channel length of less than twice the spatial spread of the AP's rising phase (vertical dashed line), the signal amplitudes were nearly equivalent, implying that the optimum electrode is at mid-channel. When channel lengths exceed twice the rising phase of the AP (42% for the M&L waveforms and 36% for the P&B waveforms), the optimum electrode position is offset from mid-channel, a configuration that results in greater signal amplitudes over a wide range of channel lengths compared to the centered electrode configuration. The point of divergence is seen to be exact in the triangularized AP representations (FIGS. 15C and 15D), a result that can be demonstrated mathematically. Differences in signal amplitude between the optimum and centered configurations (lower-most line in each plot) peak at about 80% of the M&L wavelength and 50% of the P&B wavelength.

In FIG. 16A, an electrode located 21% of the M&L wavelength from the channel exit is optimally configured to record an M&L waveform propagating in the right to left direction (labeled as "normal" in this figure), and in FIG. 16B, the offset is poorly configured for the same waveform propagating in the left to right direction (labeled as "reverse" in this figure) through the same channel, where the maximum recorded signal is 45% of the AP peak smaller than those recorded when this AP propagates in the "normal" direction. Also, there is a marked difference in the shape of the second difference profile (X-axis is time as indicated) recorded at the electrode site as the AP passes through the channel. For APs traveling in the "normal" direction, the second difference profile has a large middle positive peak flanked by two much smaller negative phases, whereas for those traveling in the "reverse" direction, the profile has a reduced positive peak followed by a negative peak of approximately equal magnitude. Differences in the amplitudes and shape of recorded signals can be used to selectively detect APs traveling in a specific direction. Channel length was 80% of the M&L wavelength in this simulation.

FIG. 17A is for an M&L waveform; FIG. 17B is for a triangularized representation of the M&L waveform of FIG. 17A; FIG. 17C is for a P&B waveform; and FIG. 17D is for a triangularized representation of the P&B waveform of FIG. 17C. Channels are configured with the electrode in the optimum position (e.g., 21% and 18% from the channel exit for the M&L and P&B waveforms, respectively) for APs traveling in the right to left direction through the channel (see also FIG. 16A). Identical APs traveling in the opposite direction are markedly attenuated by comparison, with differences in signal amplitude increasing for longer channel lengths. As channel lengths approach the AP wavelength (vertical dashed lines), these differences approach 60% and 40% of the AP peak for the M&L and P&B waveforms, respectively.

FIG. 18A is for an M&L waveform, and FIG. 18B is for a P&B waveform. For the optimum electrode configuration, the electrode was located at 21% of the M&L wavelength and 18% of the P&B wavelength from the channel exit. Actual target action potentials would need to exceed those used to optimize the electrode position by more than 1.7 times the M&L wavelength and 2.2 times P&B wavelength (dashed vertical lines in FIGS. 18A and 18B, respectively) before this ideal offset configuration would perform worse than the centered design.

DETAILED DESCRIPTION

Embodiments of the subject invention provide devices, systems, and methods for recording action potential (AP) from a nerve. A device can include, for example, a cuff or a microchannel to be used to record an AP from a nerve (e.g., a nerve of a subject such as a mammalian subject (e.g., a human subject)). An electrode can be included (e.g., within a channel or lumen or channel lumen of the cuff or microchannel), and the (recording) electrode can be offset or off-center (i.e., not located mid-channel within the recording cuff or microchannel). Related art recording devices position the electrode mid-channel (centered) within the cuff or microchannel.

When the electrode is positioned offset, as in embodiments of the subject invention, this enhances recorded signals in axons conducting in the head-to-tail direction and, simultaneously, attenuates those traveling in the opposite, tail-to-head direction. Thus, an off-centered recording electrode transforms a traditional nerve cuff or microchannel into one that is inherently equipped to distinguish afferent (sensory) from efferent (motor) or efferent from afferent neural activity simply based on the head-to-tail orientation of the cuff (or microchannel) electrode on the nerve.

Figure 1:
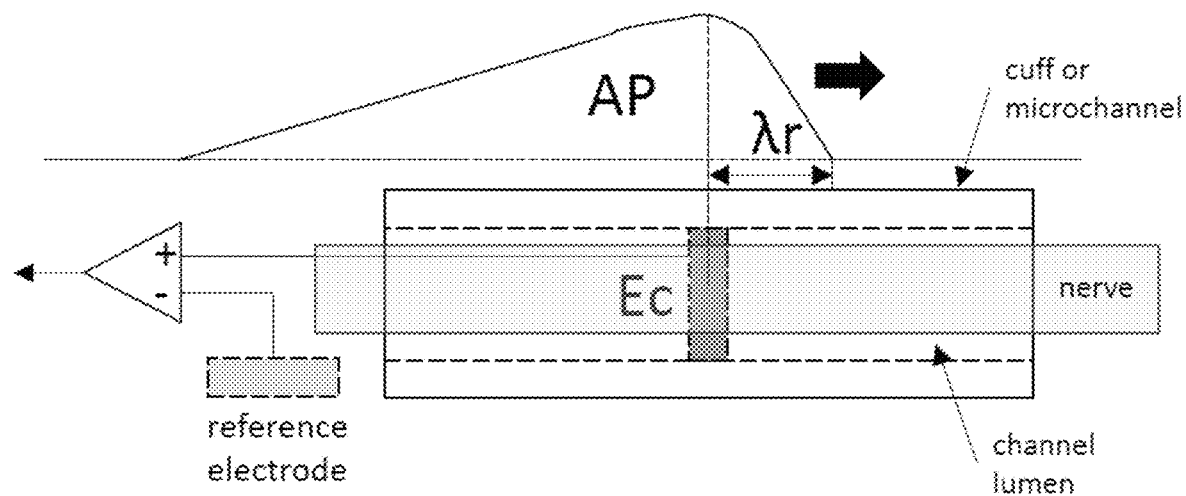
FIG. 1 shows a cross-sectional side view of a recording cuff or microchannel with its electrode (labeled Ec) at mid-channel. For illustrative purposes only, the AP is depicted as traveling outside the cuff or microchannel; in reality, the AP travels inside the nerves confined within the lumen of the cuff/channel.
Figure 2:
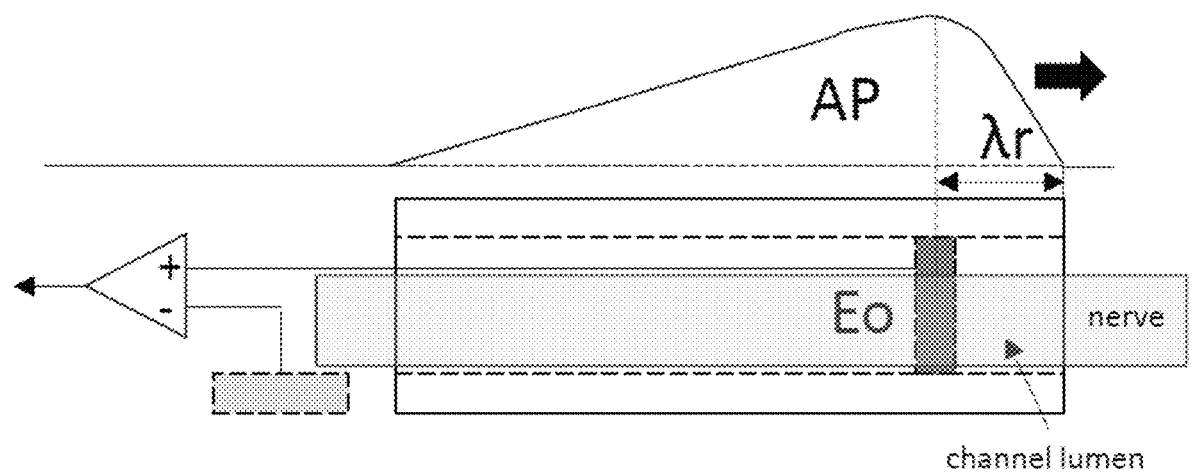
FIG. 2 shows a cross-sectional side view of a recording cuff or microchannel with its electrode (labeled Eo) in an offset position, according to an embodiment of the subject invention. For illustrative purposes only, the AP is depicted as traveling outside the cuff or microchannel; in reality, the AP travels inside the nerves confined within the lumen of the cuff/channel.
Figure 3:
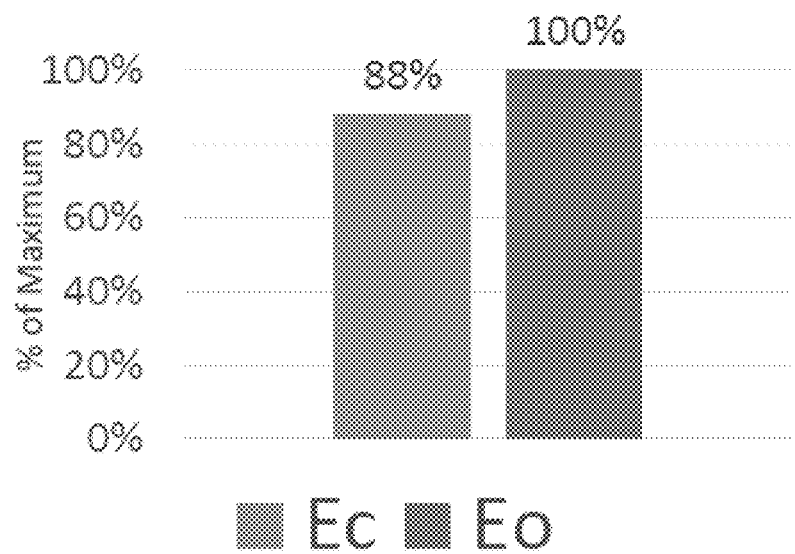
FIG. 3 shows a bar graph of the recorded signal amplitude due to action potential (AP) traveling from left-to-right through the cuff for the electrode Ec of FIG. 1 (left bar) and for the electrode Eo of FIG. 2 (right side). When the electrode is located mid-channel, as in FIG. 1, the recorded signal amplitude due to AP is only 88% of the maximum value that is achieved when the electrode is shifted, as in FIG. 2, in the direction of AP propagation so that the distance from the cuff/channel end equals the length of the rising phase ($\lambda r$). The offset electrode will always record a larger signal when cuff/channel length is at least twice $\lambda r$; otherwise, for cuffs/channels shorter than this, the centered configuration can give better results.

FIG. 1 shows a cross-sectional side view of a recording cuff or microchannel with its electrode (labeled Ec) at mid-channel, and FIG. 2 shows a cross-sectional side view of a recording cuff or microchannel with its electrode (labeled Eo) in an offset position, according to an embodiment of the subject invention. For illustrative purposes only, the APs are depicted in FIGS. 1 and 2 as traveling outside the cuff or microchannel; in reality, the AP travels inside the nerves confined within the lumen of the cuff/channel. FIG. 3 shows a bar graph of the recorded signal amplitude due to AP traveling from left-to-right through the cuff for the electrode Ec of FIG. 1 (left bar) and for the electrode Eo of FIG. 2 (right side). When the electrode is located mid-channel, as in FIG. 1, the recorded signal amplitude due to AP is only 88% of the maximum value that is achieved when the electrode is shifted, as in FIG. 2, in the direction of AP propagation so that the distance from the cuff/channel end equals the length of the rising phase ($\lambda r$). The offset electrode will always record a larger signal when cuff/channel length is at least twice $\lambda r$; otherwise, for cuffs/channels shorter than this, the centered configuration may give better results.

Figure 4A:
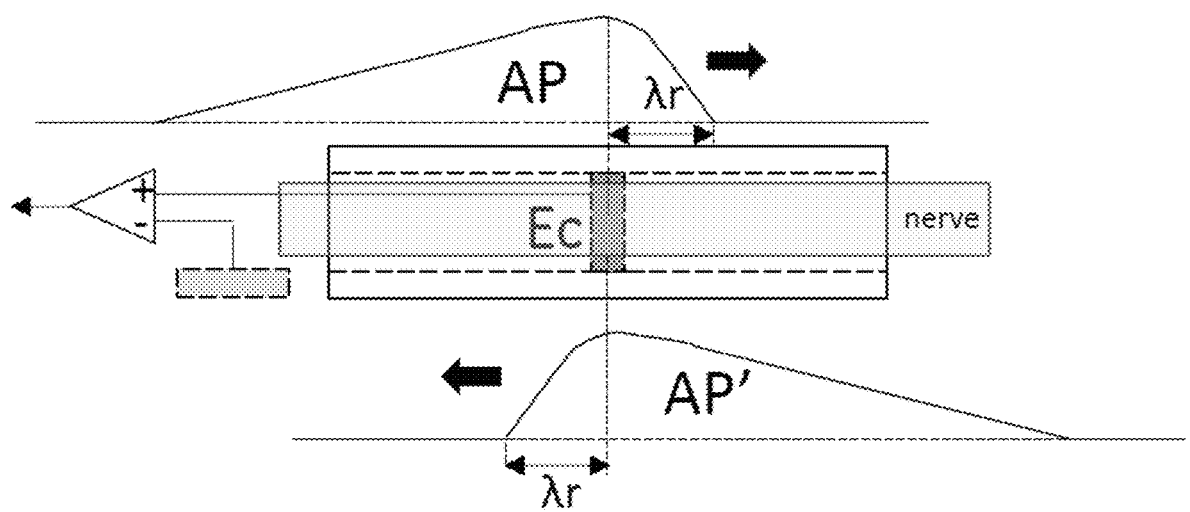
FIG. 4A shows a cross-sectional side view of a recording cuff or microchannel with its electrode (labeled Ec) at mid-channel, along with the AP depicted for both directions (left-to-right, labeled AP, and right-to-left, labeled AP'). For illustrative purposes only, the APs are depicted as traveling outside the cuff or microchannel; in reality, the APs travel inside the nerves confined within the lumen of the cuff/channel.
Figure 4B:
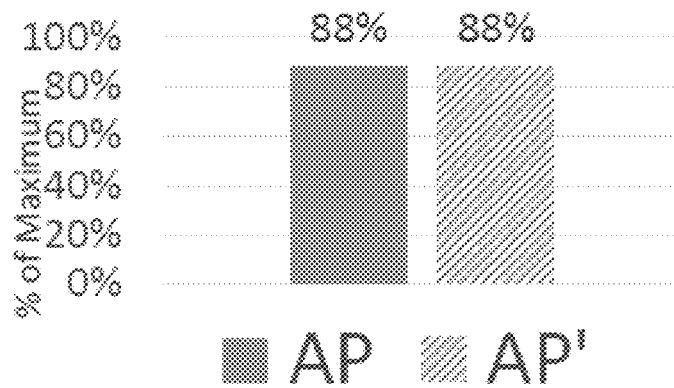
FIG. 4B shows a bar graph of the recorded signal amplitude due to AP traveling from left-to-right (left side of graph) and also due to AP' traveling from right-to-left (right side of graph) through the cuff for the electrode Ec of FIG. 4A. When the electrode is located mid-channel, as in FIG. 4A, the recorded signal amplitude due to AP is only 88% of the maximum value that is achieved for AP (left-to-right) when the electrode is shifted, as in FIG. 5A, in the direction of AP propagation so that the distance from the cuff/channel end equals the length of the rising phase ($\lambda r$).
Figure 5A:
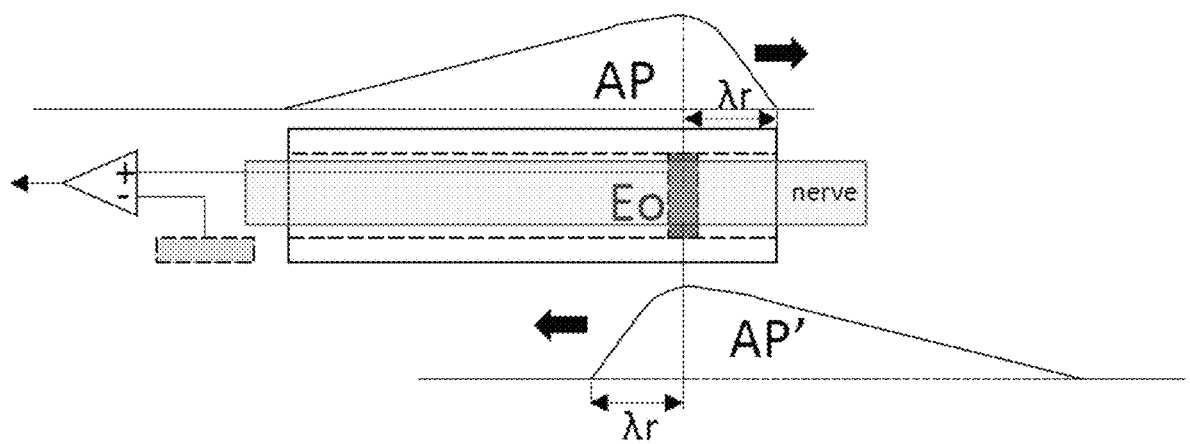
FIG. 5A shows a cross-sectional side view of a recording cuff or microchannel with its electrode (labeled Eo) in an offset position, according to an embodiment of the subject invention, along with the AP depicted for both directions (left-to-right, labeled AP, and right-to-left, labeled AP'). For illustrative purposes only, the APs are depicted as traveling outside the cuff or microchannel; in reality, the APs travel inside the nerves confined within the lumen of the cuff/channel.
Figure 5B:
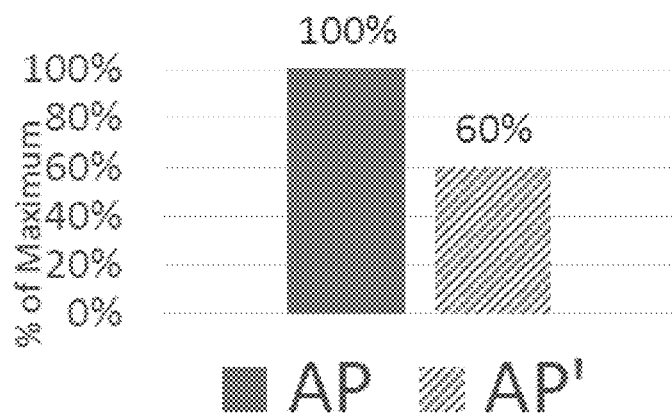
FIG. 5B shows a bar graph of the recorded signal amplitude due to AP traveling from left-to-right (left side of graph) and also due to AP' traveling from right-to-left (right side of graph) through the cuff for the electrode Eo of FIG. 5A. The recorded signal amplitude due to AP is at its maximum while the recorded signal amplitude for AP' is only 60% of the maximum.

FIG. 4A shows a cross-sectional side view of a recording cuff or microchannel with its electrode (labeled Ec) at mid-channel, along with the AP depicted for both directions (left-to-right, labeled AP, and right-to-left, labeled AP'); and FIG. 5A shows a cross-sectional side view of a recording cuff or microchannel with its electrode (labeled Eo) in an offset position, according to an embodiment of the subject invention, along with the AP depicted for both directions (left-to-right, labeled AP, and right-to-left, labeled AP'). For illustrative purposes only, the APs are depicted in FIGS. 4A and 5A as traveling outside the cuff or microchannel; in reality, the APs travel inside the nerves confined within the lumen of the cuff/channel. FIG. 4B shows a bar graph of the recorded signal amplitude due to AP traveling from left-to-right (left side of graph) and also due to AP' traveling from right-to-left (right side of graph) through the cuff for the electrode Ec of FIG. 4A. When the electrode is located mid-channel, as in FIG. 4A, the recorded signal amplitude due to AP is only 88% of the maximum value that is achieved for AP (left-to-right) when the electrode is shifted, as in FIG. 5A, in the direction of AP propagation so that the distance from the cuff/channel end equals the length of the rising phase ($\lambda r$). FIG. 5B shows a bar graph of the recorded signal amplitude due to AP traveling from left-to-right (left side of graph) and also due to AP' traveling from right-to-left (right side of graph) through the cuff for the electrode Eo of FIG. 5A. The recorded signal amplitude due to AP is at its maximum while the recorded signal amplitude for AP' is only 60% of the maximum.

In many embodiments, two recording electrodes can be used, each positioned in an offset (off-center) location along a cuff or microchannel. Each recording electrode can be positioned the same distance from its closest channel end, though embodiments are not limited thereto. For example, each recording electrode can be positioned a distance of $\lambda r$ (the rising phase of the AP; that is, the width of the wave from its peak to zero in the direction of propagation, as depicted in the figures).

Figure 6A:
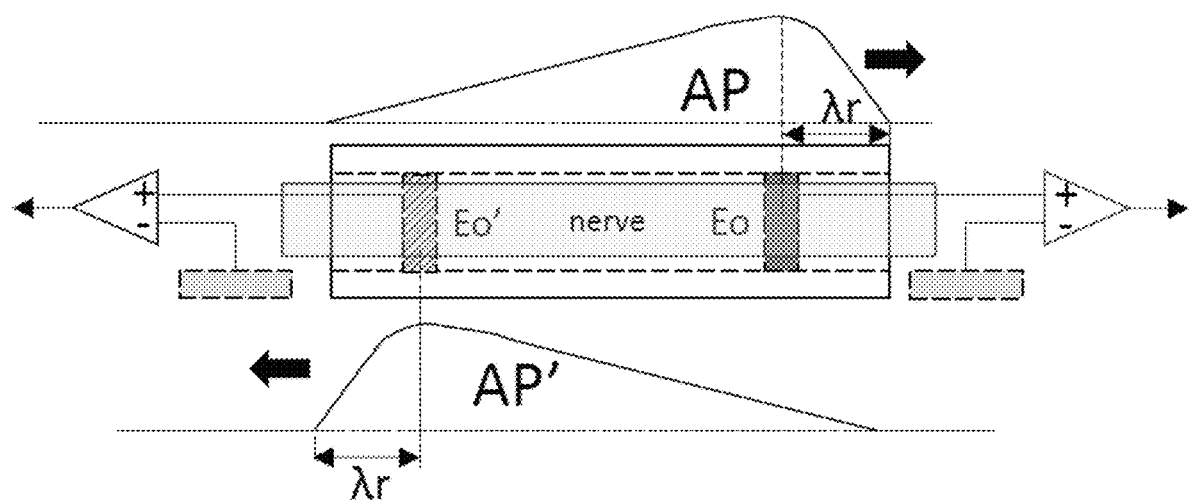
FIG. 6A shows a cross-sectional side view of a dual cuff or microchannel electrode design, which includes a cuff or microchannel configured with two offset electrodes (labeled as Eo and Eo') positioned a distance λr from each end, according to an embodiment of the subject invention. This configuration maximizes the recorded signal for action potentials traveling in opposite directions through the restriction. This design is capable of discriminating between action potentials traveling in opposite directions through the cuff/channel, and the electrodes can be positioned at an optimum distance of λr from each channel end. This configuration enables 100% amplitude recordings to be obtained at Eo and Eo' when AP and AP' pass through the channel, respectively. This configuration can also simultaneously achieve a 40% attenuation of AP and AP' at Eo' and Eo, respectively (see also FIG. 5B). Thus, the dual offset electrode offset cuff or microchannel can provide a basis upon which to discriminate action potentials traveling in opposite directions through the restricted space.
Figure 6B:
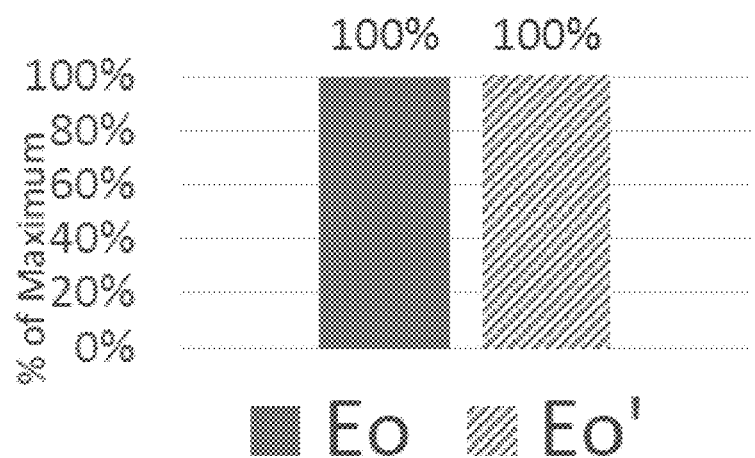
FIG. 6B shows a bar graph of the recorded signal amplitude due to AP traveling from left-to-right recorded by Eo (left side of graph) and also due to AP' traveling from right-to-left recorded by Eo' (right side of graph) in the cuff or microchannel of FIG. 6A. The recorded signal amplitude due to AP and AP' can be maximized by Eo and Eo', respectively.

FIG. 6A shows a cross-sectional side view of a dual cuff or microchannel electrode design, which includes a cuff or microchannel configured with two offset electrodes (labeled as Eo and Eo') positioned a distance $\lambda r$ from each end, according to an embodiment of the subject invention. This configuration maximizes the recorded signal for action potentials traveling in opposite directions through the restriction. This design is capable of discriminating between action potentials traveling in opposite directions through the cuff/channel, and the electrodes can be positioned at an optimum distance of $\lambda r$ from each channel end. This configuration enables 100% amplitude recordings to be obtained at Eo and Eo' when AP and AP' pass through the channel, respectively. This configuration can also simultaneously achieve a 40% attenuation of AP and AP' at Eo' and Eo, respectively (see also FIG. 5B). Thus, the dual offset electrode offset cuff or microchannel can provide a basis upon which to discriminate action potentials traveling in opposite directions through the restricted space. FIG. 6B shows a bar graph of the recorded signal amplitude due to AP traveling from left-to-right recorded by Eo (left side of graph) and also due to AP' traveling from right-to-left recorded by Eo' (right side of graph) in the cuff or microchannel of FIG. 6A. The recorded signal amplitude due to AP and AP' can be maximized by Eo and Eo', respectively.

Figure 7:
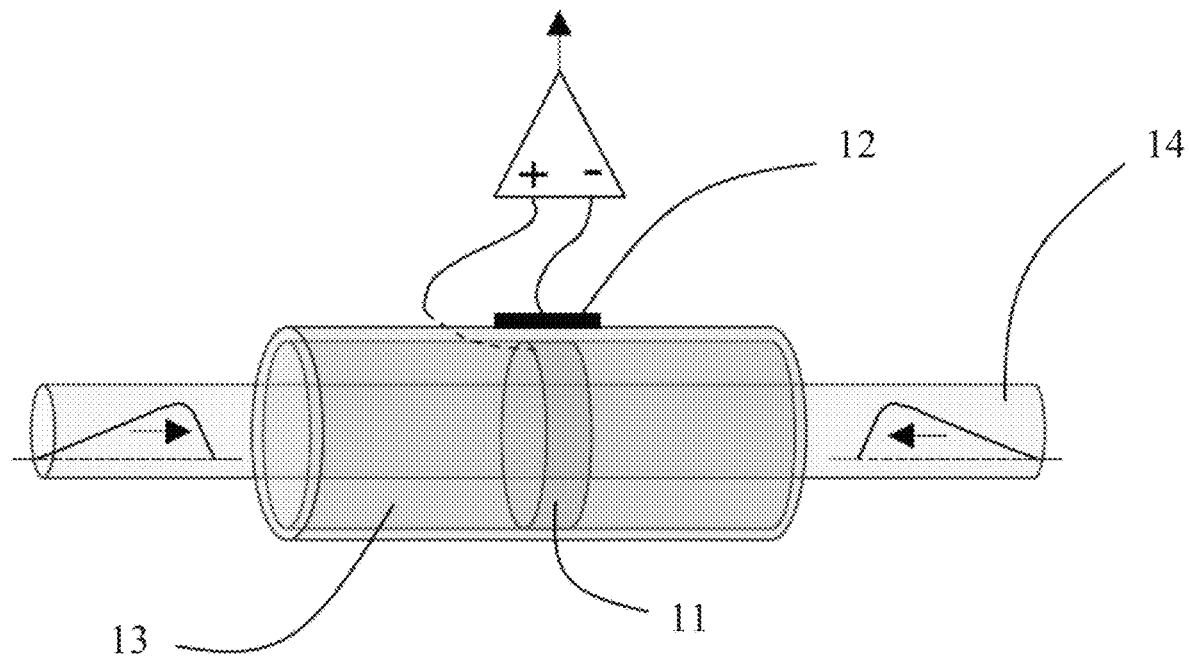
FIG. 7 shows a view of a cuff having the electrode at mid-channel.
Figure 8:
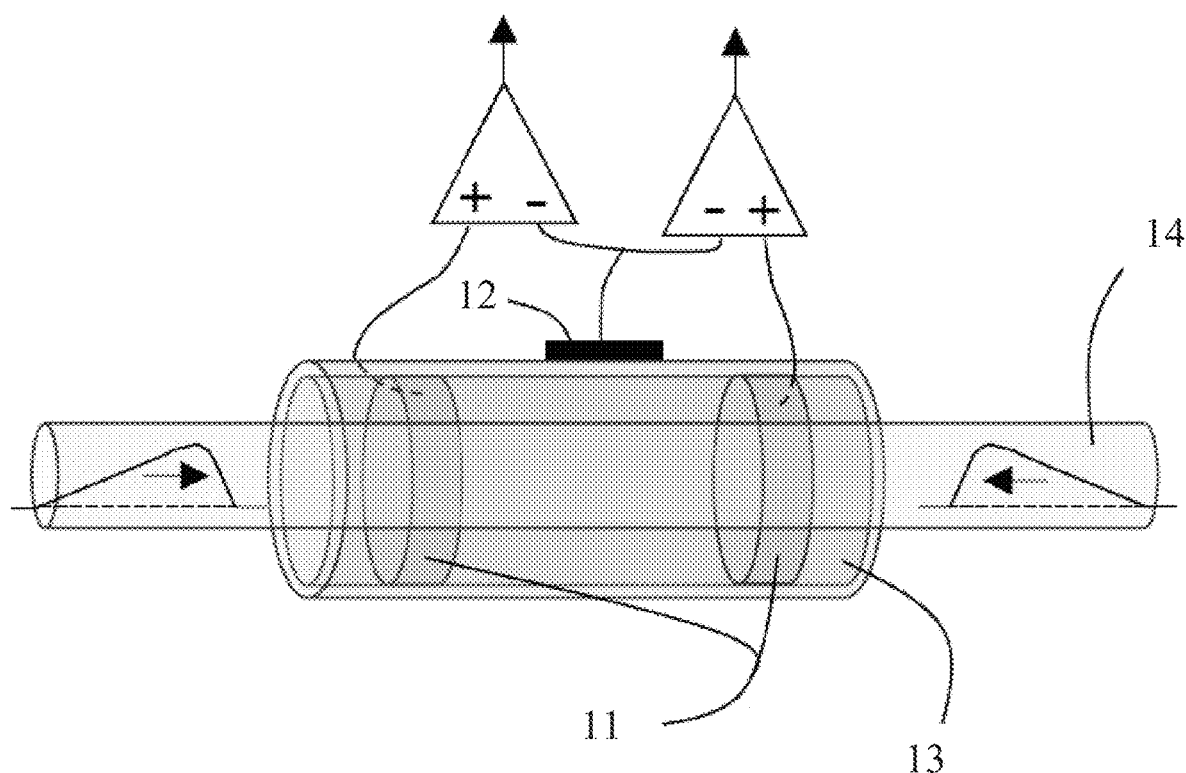
FIG. 8 shows a view of a cuff having dual offset electrodes, according to an embodiment of the subject invention.

FIG. 7 shows a view of a cuff having the electrode at mid-channel, and FIG. 8 shows a view of a cuff having dual offset electrodes, according to an embodiment of the subject invention. Referring to FIG. 8, in an embodiment, a recording device can include a cuff 13 (e.g., a cuff made of insulative material such as silicone or polyimide), a reference electrode 12, and a biocompatible electrode 11. The reference electrode can be sutured or bonded (e.g., silicone-bonded) to an outside wall of the cuff 13. The biocompatible electrode can include, for example, one or more of gold, platinum, and iridium, though embodiments are not limited thereto. The cuff can be placed around a nerve 14, which can be a mixed nerve conducting APs in both directions.

Figure 9A:
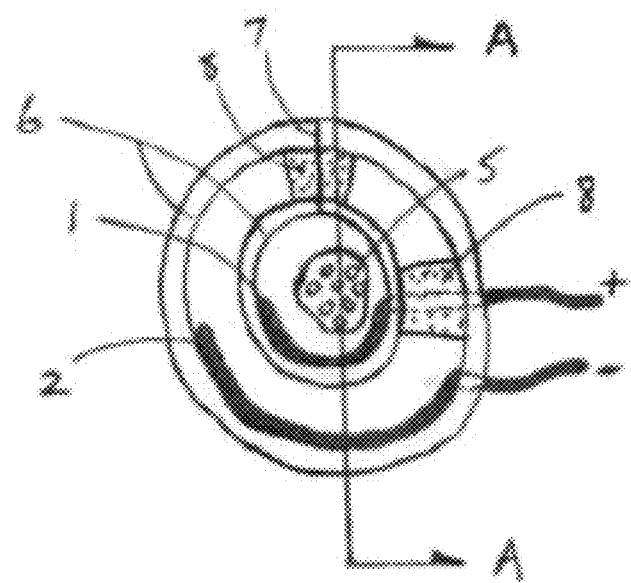
FIG. 9A shows a cross-sectional front view of a cuff with dual offset electrodes according to an embodiment of the subject invention.
Figure 9B:
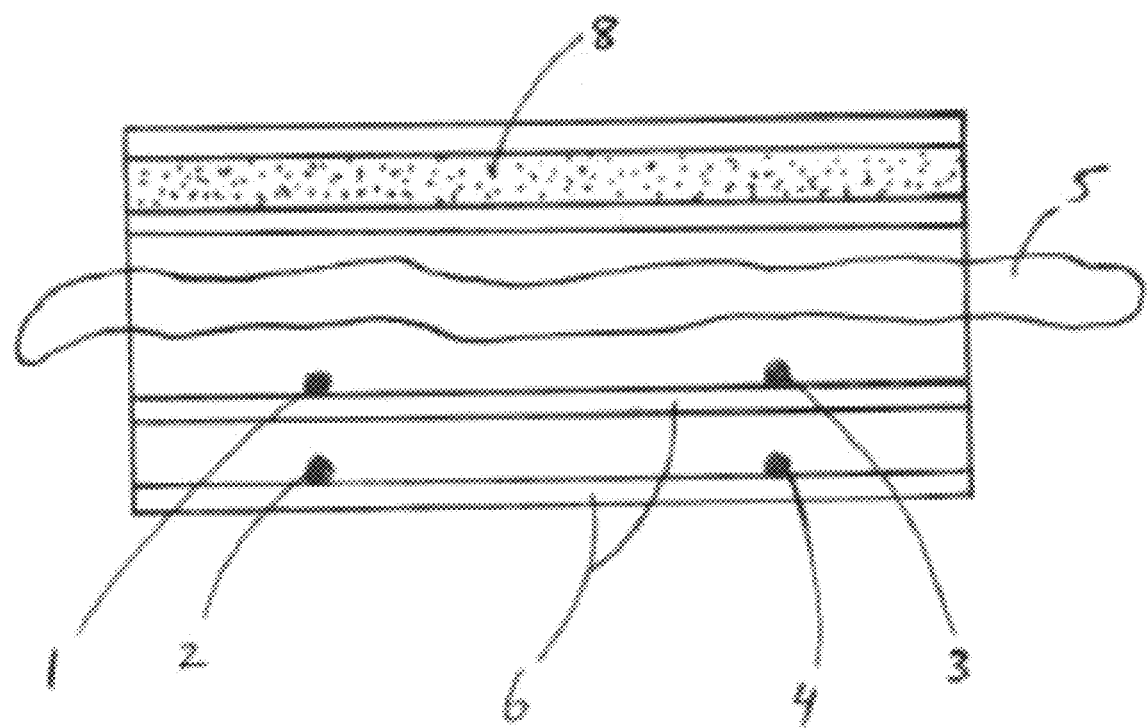
FIG. 9B shows a cross-sectional side view taken along line A-A in FIG. 9B.
Figure 10A:
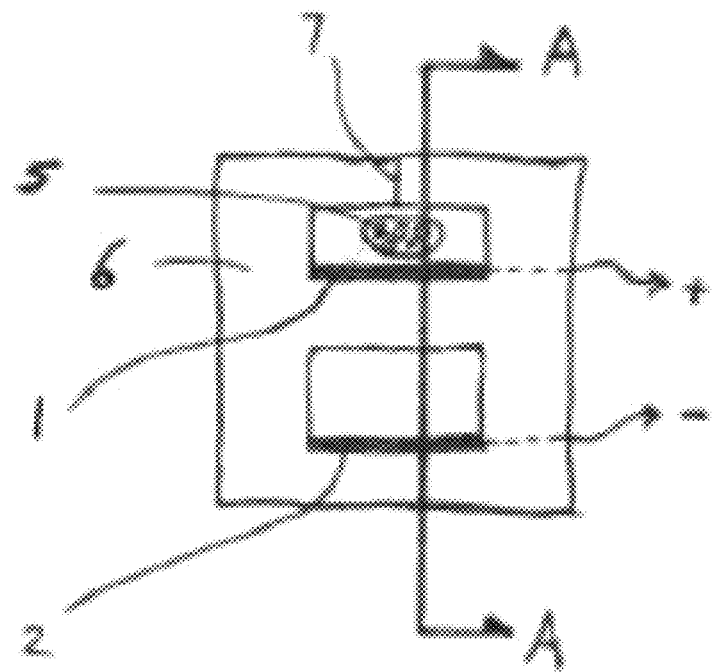
FIG. 10A shows a cross-sectional front view of a microchannel with dual offset electrodes according to an embodiment of the subject invention.
Figure 10B:
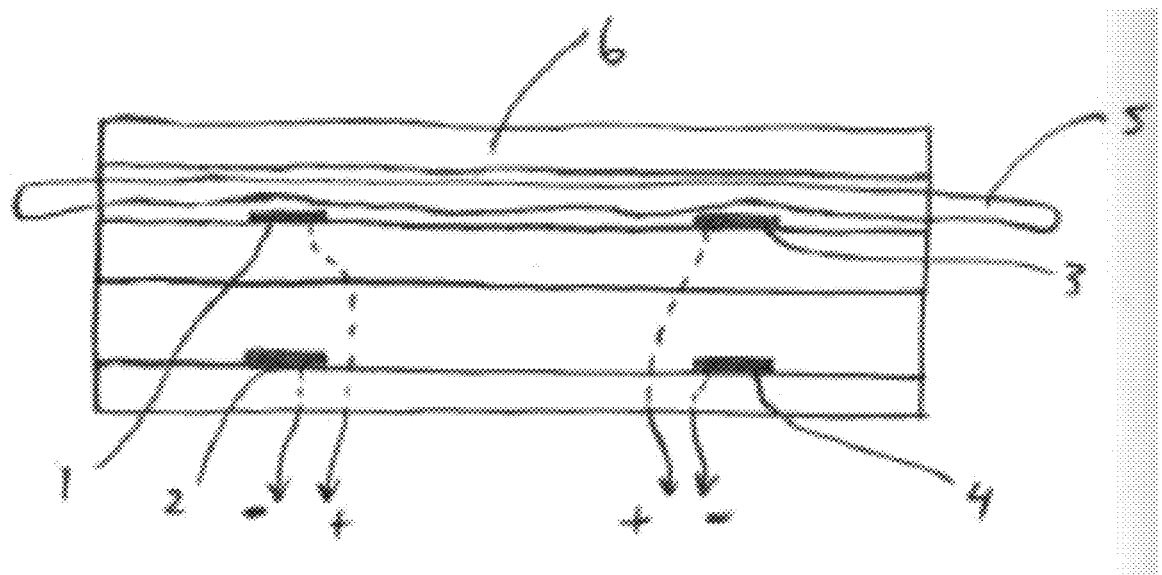
FIG. 10B shows a cross-sectional side view taken along line A-A in FIG. 10B.

FIG. 9A shows a cross-sectional front view of a cuff with dual offset electrodes according to an embodiment of the subject invention, and FIG. 9B shows a cross-sectional side view taken along line A-A in FIG. 9B. Also, FIG. 10A shows a cross-sectional front view of a microchannel with dual offset electrodes according to an embodiment of the subject invention, and FIG. 10B shows a cross-sectional side view taken along line A-A in FIG. 10B. Referring to FIGS. 9A, 9B, 10A, and 10B, in some embodiments, a dual offset electrode recording device (for noise cancellation) can include two electrodes 1,3, two reference electrodes 2,4, and a substrate 6 (e.g., a flexible substrate such as silicone or polyimide). Although two reference electrodes are shown 2,4, this is for exemplary purposes only, and in many cases only one reference electrode need be present (see also FIG. 8). The device can also include a slit 7 that permits opening of the cuff or microchannel for insertion of nerve, and/or a bonding bridge 8 connecting concentric tubes within the cuff. The cuff or microchannel can be provided around a nerve or nerve strand 5 for AP recording.

In certain aspects, embodiments of the subject invention are similar to traditional nerve cuff technology for neural recording. However, a key difference is the placement of the recording electrode. If one end of a nerve cuff were designated the "head" and the other the "tail", then for a neural signal propagating in the direction of head-to-tail, the recording electrode can be positioned nearer the "tail" of the cuff or microchannel. Embodiments of the subject invention have many advantageous applications, including any application involving recording from mixed nerves containing both sensory and motor fibers. Detection of motor activity can be achieved by placing a cuff or microchannel with its "head" oriented proximally, while detection of sensory activity can be accomplished by flipping the device on the nerve so as to orient the "tail" in the proximal direction. Certain embodiments include two off-centered electrodes for the simultaneous and separate detection of sensory and motor activity in one device. The two-electrode iteration can have one electrode situated nearer the "head" end of the device with the other placed nearer the "tail" (see also FIGS. 8, 9A, and 10A, and 10B).

Most nerves contain a mix of afferent and efferent axons, and the ability to easily distinguish between these two different signal types is essential to the proper functioning of neural interface systems. One way to achieve this is through multiple electrode contacts within the cuff that record identical signals having a slight time delay between them that enables their directionality (and speed) to be determined using additional on- or off-board signal analysis software. This can also be accomplished without the need for more than one electrode or the need to process signal delays to determine signal directionality. Detection of a signal at the off-centered recording electrode itself implies directionality, as those propagating in the opposite direction would simply not be detected.

The subject invention includes, but is not limited to, the following exemplified embodiments.

Embodiment 1. A device for recording neural activity, the device comprising:
a substrate to be positioned on a nerve (or nerve fiber) and comprising a channel formed therewithin; and
a first recording electrode disposed within the channel for recording neural activity of the nerve (or nerve fiber),
the first recording electrode being positioned in an offset (non-centered) position with respect to a length of the channel (i.e., closer to one end of the channel than to the other end of the channel).

Embodiment 2. The device according to embodiment 1, the first recording electrode being positioned closer to one end of the channel than to a center point of the channel with respect to the length of the channel (and being positioned closer to the end of the channel that is at the end or "tail" of the propagating direction of an action potential (AP), to be measured by the first recording electrode, of the nerve on which the substrate is (to be) positioned).

Embodiment 3. The device according to any of embodiments 1-2, the length of the channel being greater than two times a spatial spread of a rising phase of an action potential (AP) of the nerve on which the substrate is (to be) positioned.

Embodiment 4. The device according to any of embodiments 1-3, the first recording electrode being positioned a first distance from an end of the channel, the first distance being equal to a spatial spread of a rising phase of an AP of the nerve on which the substrate is (to be) positioned.

Embodiment 5. The device according to any of embodiments 1-4, further comprising a second recording electrode disposed within the channel for recording neural activity of the nerve (or nerve fiber),
the second recording electrode being positioned in an offset (non-centered) position with respect to the length of the channel (i.e., closer to one end of the channel than to the other end of the channel).

Embodiment 6. The device according to embodiment 5, the channel comprising a first end and a second end,
the first recording electrode being positioned closer to the first end of the channel than to the second end of the channel, and
the second recording electrode being positioned closer to the second end of the channel than to the first end of the channel.

Embodiment 7. The device according to any of embodiments 5-6, the second recording electrode being positioned closer to one end of the channel than to a center point of the channel with respect to the length of the channel (and being positioned closer to the end of the channel that is at the end or "tail" of the propagating direction of an action potential (AP), to be measured by the second recording electrode, of the nerve on which the substrate is (to be) positioned).

Embodiment 8. The device according to any of embodiments 5-7, the second recording electrode being positioned a second distance from an end of the channel, the second distance being equal to a spatial spread of a rising phase of an AP of the nerve on which the substrate is (to be) positioned.

Embodiment 9. The device according to embodiment 5, the channel comprising a first end and a second end,
the first recording electrode being positioned a first distance from the first end of the channel, the first distance being equal to a spatial spread of a rising phase of an AP of the nerve on which the substrate is (to be) positioned, and
the second recording electrode being positioned a second distance from the second end of the channel, the second distance being equal to the first distance.

Embodiment 10. The device according to any of embodiments 5-9, the second recording electrode comprising at least one of silver, gold, platinum, and iridium.

Embodiment 11. The device according to any of embodiments 5-10, the second recording electrode comprising a platinum/iridium alloy.

Embodiment 12. The device according to any of embodiments 1-11, the first recording electrode comprising at least one of silver, gold, platinum, and iridium.

Embodiment 13. The device according to any of embodiments 1-12, the first recording electrode comprising a platinum/iridium alloy.

Embodiment 14. The device according to any of embodiments 1-13, the substrate being a flexible substrate.

Embodiment 15. The device according to any of embodiments 1-14, the substrate comprising at least one of silicone and polyimide.

Embodiment 16. The device according to any of embodiments 1-15, the substrate further comprising a slit to permit opening of the substrate for insertion of the nerve (or nerve fiber).

Embodiment 17. The device according to any of embodiments 1-16, the substrate further comprising a bonding bridge connecting conductive concentric portions within the substrate to each other.

Embodiment 18. The device according to any of embodiments 1-17, the substrate being a cuff.

Embodiment 19. The device according to any of embodiments 1-17, the substrate being a microchannel.

Embodiment 20. The device according to any of embodiments 1-19, further comprising a first reference electrode in electrical contact with the first recording electrode.

Embodiment 21. The device according to any of embodiments 5-19, further comprising a first reference electrode in electrical contact with the first recording electrode and the second recording electrode.

Embodiment 22. The device according to any of embodiments 5-19, further comprising: a first reference electrode in electrical contact with the first recording electrode; and a second reference electrode in electrical contact with the second recording electrode.

Embodiment 23. The device according to embodiment 22, the first reference electrode being electrically insulated from the second reference electrode.

Embodiment 24. The device according to any of embodiments 20-23, the first reference electrode (and second reference electrode, if present) being disposed on an outer wall of the substrate.

Embodiment 25. The device according to embodiment 24, the first reference electrode (and second reference electrode, if present) being sutured to the outer wall of the substrate.

Embodiment 26. A method of recording neural activity of a nerve (or nerve fiber), the method comprising:

providing the recording device according to any of embodiments 1-25;

placing the substrate of the recording device around the nerve (or nerve fiber); and recording the neural activity from the nerve (or nerve fiber) using the recording device.

Embodiment 27. The method according to embodiment 26, recording the neural activity comprising using the first recording electrode to record at least one characteristic of a first AP from the nerve.

Embodiment 28. The method according to any of embodiments 26-27, recording the neural activity comprising using the second recording electrode (if present) to record at least one characteristic of a second AP from the nerve, the second AP being different from the first AP.

Embodiment 29. The method according to embodiment 28, the first AP being an afferent AP and the second AP being an efferent AP.

Embodiment 30. The method according to embodiment 28, the first AP being an efferent AP and the second AP being an afferent AP.

Embodiment 31. The method according to any of embodiments 26-30, the second recording electrode being present, the nerve being a mixed nerve, and the method further comprising using the first recording electrode and the second recording electrode to distinguish afferent APs of the mixed nerve from efferent APs of the mixed nerve.

Embodiment 32. The method according to embodiment 31, the first recording electrode and the second recording electrode distinguishing afferent APs of the mixed nerve from efferent APs of the mixed nerve based on a comparison of an amplitude of an AP recorded by each (higher amplitude recorded by the first recording electrode indicating that the AP propagated in a direction from the second recording electrode to the first recording electrode, and vice versa).

A greater understanding of the embodiments of the present invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

EXAMPLE 1

An extensive analysis was performed to demonstrate the advantages of offset recording electrodes in recording devices, according to embodiments of the subject invention. Stein and Pearson previously derived a mathematical model to compute the amplitude of extracellular potentials generated by unmyelinated fibers lying inside narrow channels of finite length (R. Stein & Pearson, 1971). Later, Marks and Loeb derived a nearly identical expression for predicting the extracellular potentials generated by myelinated fibers enclosed in a channel (Marks & Loeb, 1976). The latter formulation is reproduced below:

$$v(x) = -\frac{R_e}{R_i}\left[V(x) - \left(1 - \frac{x}{L}\right)V(0) - \left(\frac{x}{L}\right)V(L)\right] \quad (1)$$

where v(x) is the extracellular potential, V(x) the transmembrane potential of the active fiber within the channel, V(0) and V(L) the transmembrane voltages at the channel's entrance and exit, respectively, L the channel length, x is an axial position within the channel, $R_e$ the longitudinal resistance of the extracellular media surround the active fiber, and $R_i$ the longitudinal resistance of the active fiber's axoplasm.

The bracketed term in Equation 1 will herein be referred to as the "second difference" term or "$2^{nd}$ Difference" term to be consistent with the terminology originally assigned by Stein and Pearson (R. Stein & Pearson, 1971). The $$-\frac{R_e}{R_i}$$

leading term scales the $2^{nd}$ Difference term by a ratio of the relative diameters of the active fiber and the channel and reverses its polarity. The effect of this scaling term on the extracellular signals has received thorough attention in the literature and was not considered further in this analysis, where cross sectional relationships of the channel and active fiber may be considered to remain invariant. This analysis only assumes that the extracellular restriction is sufficiently small for the assumption of axial current flow within the channel to remain valid. The $2^{nd}$ Difference term is explored here because it characterizes the interplay between an action potential (e.g., shape and conduction speed) and channel length and, more importantly for the purposes of this analysis, the position of the recording electrode within the restricted extracellular environment.

Graphically, the $2^{nd}$ Difference term may be represented on a plot of the AP's spatial profile by taking the difference between V(x) and a line drawn between the AP's amplitude at the channel's entrance and exit, V(0) and V(L), respectively. This interpretation is helpful because, for any portion of waveform contained within the channel, the maximum signal amplitude is readily obtained as well as the axial position within the channel where this maximum signal occurs.

Figure 11A:
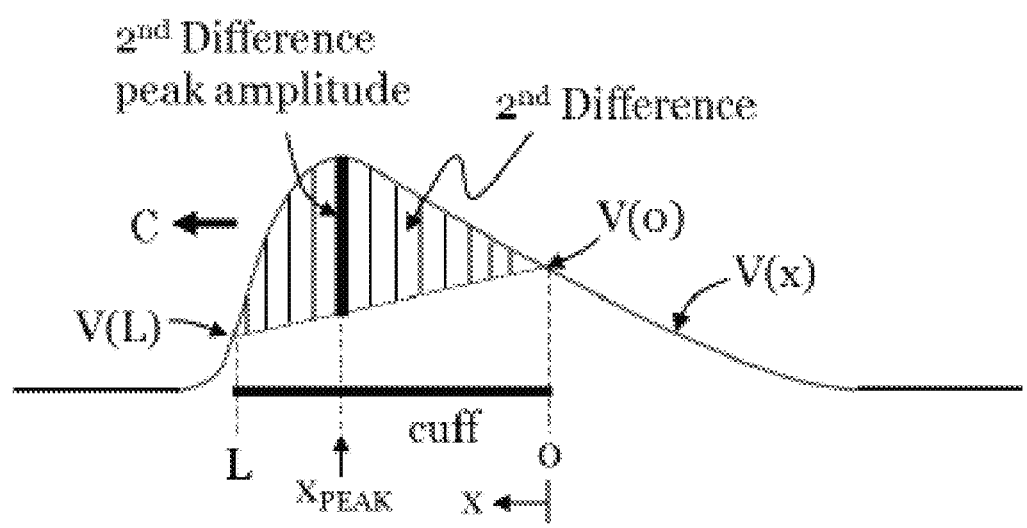
FIG. 11A shows the second difference (from Equation 1) in the shaded area in an AP waveform.
Figure 11B:
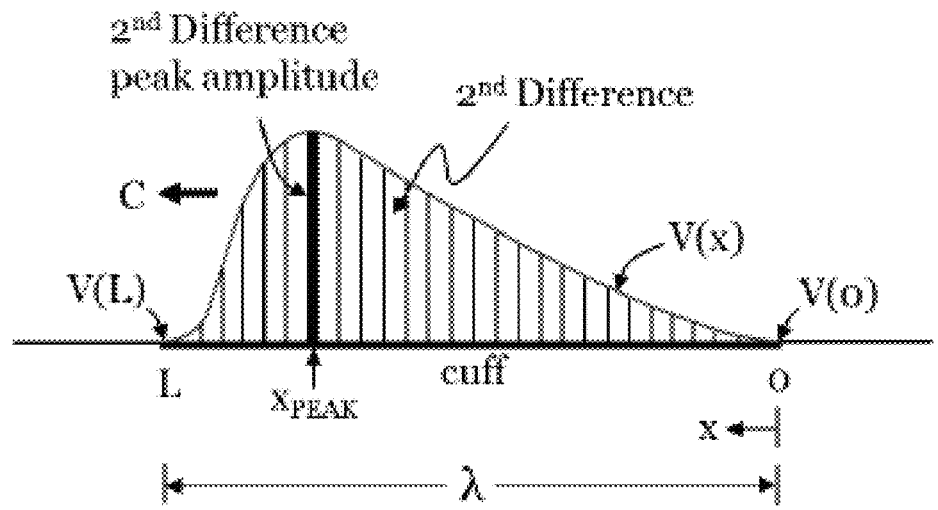
FIG. 11B shows the second difference (from Equation 1) in the shaded area in an AP waveform when channel length is the same as the AP's wavelength (L=λ).

FIGS. 11A and 11B depict an arbitrary instant in time when an AP traveling from left to right at speed C has moved into a channel of length L. The shaded portion of the waveform represents the $2^{nd}$ Difference profile at this instant because this region is obtained by subtracting the line between V(0) and V(L) from V(x) at all axial positions, x, within the channel. The darkened line represents the peak amplitude of the $2^{nd}$ Difference, $2^{nd}$ Diff$_{PEAK}$, which occurs at position $x_{PEAK}$ in the channel. This exercise may be repeated for each instant in time as the AP moves through the channel to readily determine the maximum. For recording purposes, it is desirable to maximize the extracellular potentials, v(x), inside the channel. Therefore, channel designs that maximize the $2^{nd}$ Difference, or shaded areas depicted in FIGS. 11A and 11B, should be sought. It is clear from FIG. 11A that any reduction of V(0) or V(L), the AP's potential at the ends of the channel, would lower the diagonal line connecting the AP's amplitude at the channel entrance and exit and result in a larger shaded area. It may be considered whether there is a channel configuration that would eliminate the diagonal altogether as this would result in the absolute maximum $2^{nd}$ Difference profile. A diagonal of zero amplitude requires the amplitude of the AP at both ends of the channel be simultaneously zero. If the channel is equal in length to the AP wavelength, this condition is met at the instant shown in FIG. 11B, where an AP traveling from left to right at speed C lies entirely within the channel extents. At this instant, the line connecting the AP's amplitude at the channel entrance and exit is zero at all points within the channel and does not detract at all from V(x). This results in a maximum $2^{nd}$ Difference profile equal to the AP's spatial profile, with a peak equal to and coincident with the AP peak as shown.

A couple of items are worth noting at this point. Had the AP been symmetrical about its peak, the maximum would have occurred at mid-channel. However, because APs are skewed waveforms, peaking closer to their rising edge, the maximum extracellular signal occurs at locations closer to the channel exit than near the middle as shown in FIG. 11B. Given the intrinsic asymmetry of single fiber action potentials, a general result of this graphical exercise is that an offset recording electrode will always be the ideal position for situations where the channel length equals the spatial spread of the single fiber AP waveform being targeted for recording. Also, this result explains the observation that the maximum extracellular potential occurs at a location closer to the channel exit than its center (see also, e.g., FitzGerald et al., 2008). Motivated by the results of this graphical exercise, computer simulations were performed to better quantify the interplay between AP shape, channel length and electrode position.

Four action potential waveforms were analyzed (FIGS. 12A-12D). The Marks & Loeb (M&L) waveform is representative of a realistic action potential. It was borrowed by Marks and Loeb from Paintal who recorded monopolar APs generated by individual myelinated axons in cat sciatic nerves (Paintal, 1966). The Plonsey & Barr (P&B) waveform was computed using formulas given in Chapter 13 of (Plonsey & Barr, 2007); all of the references mentioned in this paragraph are hereby incorporated by reference herein in their entireties. It is included because it is more symmetrical about its peak than the M&L waveform, and symmetry, as previously noted, is expected to influence the optimum electrode placement. The triangularized waveforms are linear approximations of the M&L and P&B waveform and are included to demonstrate the significance of the spatial spread of an APs rising phase on the determination of optimum electrode position. These will also be used to derive expressions for the computing the maximum signal amplitude one could expect to record for any given AP, channel length, and electrode position. None of the action potential waveforms depicted in FIGS. 12A-12D had a hyperpolarization phase. Simulations run on those that did revealed a slight increase in signal above the AP peak amplitude for certain channel lengths and electrode positions but these were less than 1% of the AP peak and hence not reported. In all cases, each waveform was normalized to 100% of its peak amplitude and 100% of its wavelength. This enabled action potentials having different shapes to be readily compared, independent of their actual amplitude or wavelength characteristics.

Figure 12:
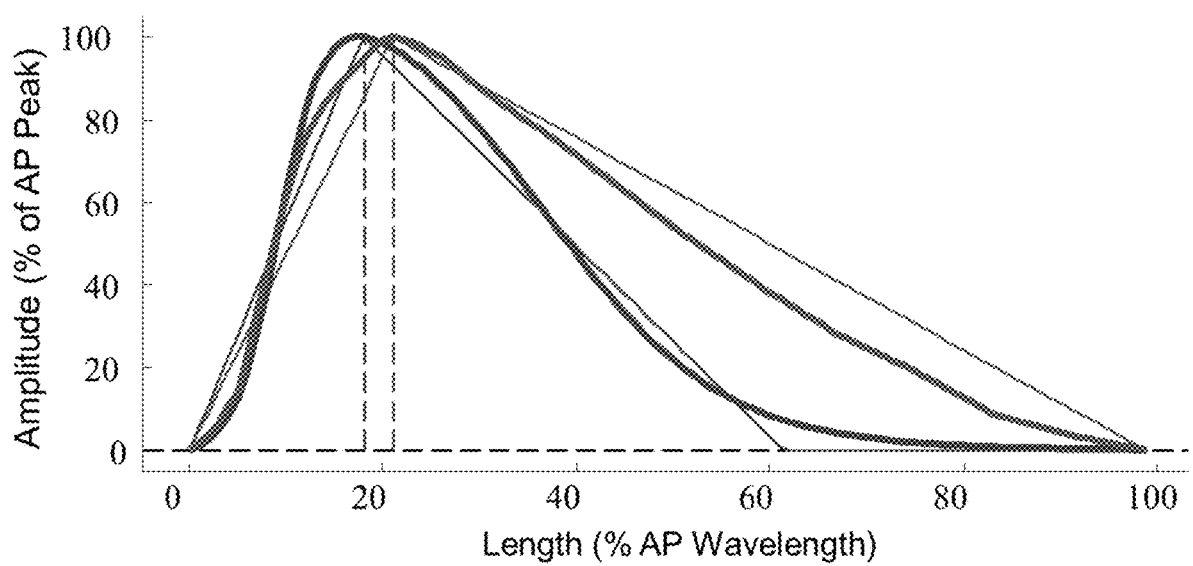
FIG. 12 shows a plot of amplitude (as a % of AP peak) along the length of a recording channel (as a % of AP wavelength). The waveforms did not have a hyperpolarization phase so wavelengths are equal to the spatial extent of their depolarization phases as shown. Waveforms were normalized by their peak amplitude and wavelength to highlight the impact of shape, particularly the degree of asymmetry, on extracellular signal amplitudes (as predicted by Equation 1). The thicker (blue) line that is lower on the right side of the plot is for the Plonsey and Barr (P&B) waveform; the thicker (red) line that is higher on the right side of the plot is for the Marks and Loeb (M&L) waveform; the thinner (blue) line that is lower on the right side of the plot is for the triangularized P&B waveform; and the thinner (red) line that is higher on the right side of the plot is for the triangularized M&L waveform. Compared to the P&B waveform, the M&L waveform is less symmetric about its peak due to its longer falling phase. Action potentials reach 100% of their peak amplitude at the end of their rising phases, which is 21% of the M&L wavelength (dashed vertical (red) line that is more to the right) and 18% of the P&B wavelength (dashed vertical (blue) line that is more the left). The triangularized representations of the M&L and P&B waveforms are included to highlight the significance of the spatial spread of an AP's rising phase in optimizing electrode position for any length cuff or channel.

FIG. 12 shows a plot of amplitude (as a % of AP peak) along the length of a recording channel (as a % of AP wavelength). The waveforms did not have a hyperpolarization phase so wavelengths are equal to the spatial extent of their depolarization phases as shown. Waveforms were normalized by their peak amplitude and wavelength to highlight the impact of shape, particularly the degree of asymmetry, on extracellular signal amplitudes (as predicted by Equation 1). The thicker (blue) line that is lower on the right side of the plot is for the P&B waveform; the thicker (red) line that is higher on the right side of the plot is for the M&L waveform; the thinner (blue) line that is lower on the right side of the plot is for the triangularized P&B waveform; and the thinner (red) line that is higher on the right side of the plot is for the triangularized M&L waveform. Compared to the P&B waveform, the M&L waveform is less symmetric about its peak due to its longer falling phase. Action potentials reach 100% of their peak amplitude at the end of their rising phases, which is 21% of the M&L wavelength (dashed vertical (red) line that is more to the right) and 18% of the P&B wavelength (dashed vertical (blue) line that is more the left). The triangularized representations of the M&L and P&B waveforms are included to highlight the significance of the spatial spread of an AP's rising phase in optimizing electrode position for any length cuff or channel.

Figure 13A:
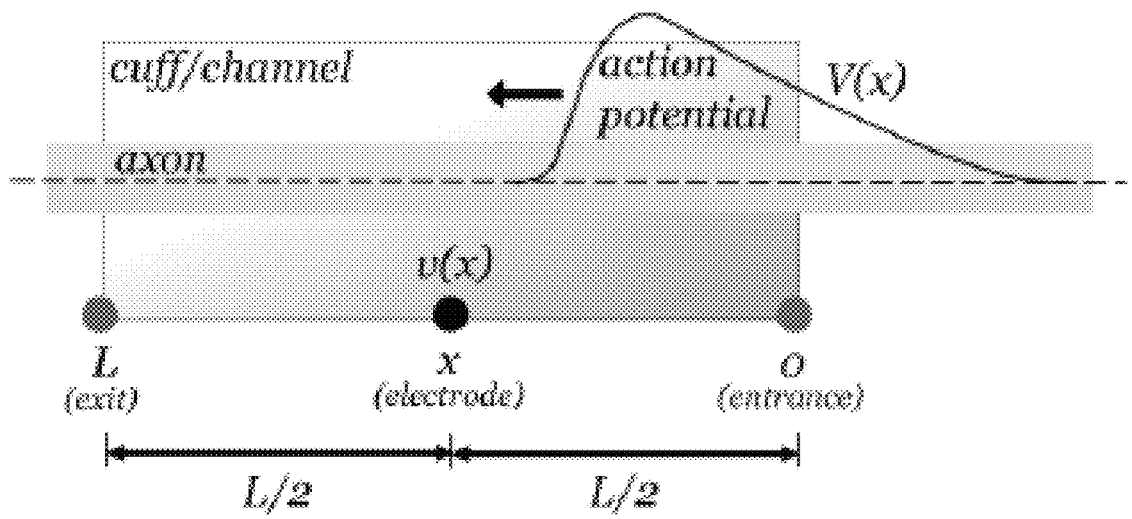
FIG. 13A shows a representation of simulations (labeled Scenario 1) in which the second difference (from Equation 1) was computed at each time step as the AP was advanced from right to left through the channel with the electrode positioned at mid-channel. The peak second difference at each time step was stored in a temporary variable.
Figure 13B:
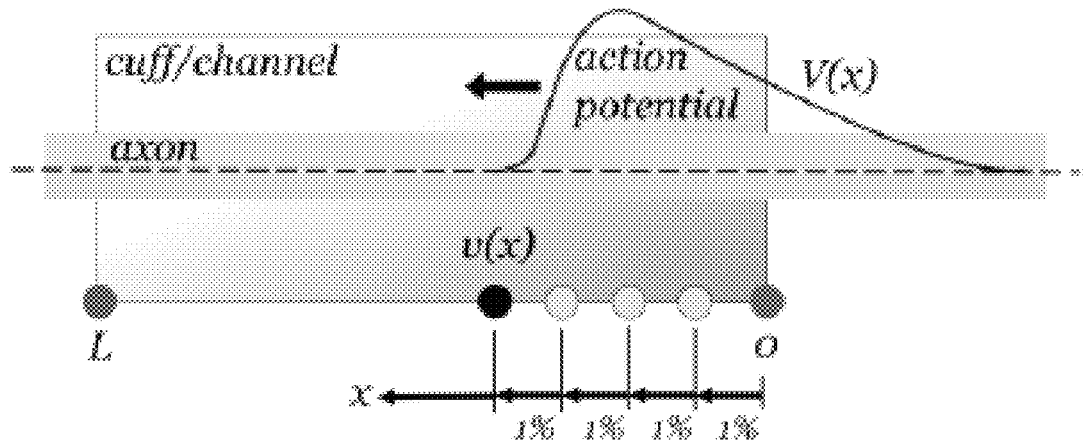
FIG. 13B shows a representation of simulations (labeled Scenario 2) in which the second difference (from Equation 1) was computed 100 times at each time step as the electrode position was incrementally varied over the length of the channel. The peak second difference and electrode position corresponding to the peak were stored in temporary variables. In both Scenario 1 (FIG. 13A) and Scenario 2, after the AP had been advanced entirely through the channel extents, the second difference peaks recorded at each time step were compared to yield a maximum second difference. In scenario 2 simulations, the electrode position corresponding to the maximum second difference served as an additional output variable.

The four APs were incrementally stepped through channels of progressively increasing length, and the $2^{nd}$ Difference computed under two different electrode position scenarios as shown in FIGS. 13A and 13B. The first scenario (FIG. 13A) computed the $2^{nd}$ Difference and recorded its peak amplitude at each time step with the electrode fixed at mid-channel, or x=L/2. A second scenario (FIG. 13B) varied the electrode position over the entire channel, from x=0 to x=L, in increments of 1% of the AP wavelength. The $2^{nd}$ Difference was calculated for each of 101 electrode positions and the peak $2^{nd}$ Difference recorded as well as the electrode position corresponding to the peak. This procedure was repeated at each time step as the AP was stepped through the channel. After the AP had passed through the channel, the largest $2^{nd}$ Difference peak was designated as the "maximum $2^{nd}$ Difference" and served as the final output variable for both sets of simulation scenarios. The electrode position where the maximum $2^{nd}$ Difference occurred, also referred here as the "optimum" position, served as an additional output variable for simulations run under the second scenario.

FIG. 13A shows a representation of simulations (labeled Scenario 1) in which the second difference (from Equation 1) was computed at each time step as the AP was advanced from right to left through the channel with the electrode positioned at mid-channel. The peak second difference at each time step was stored in a temporary variable.

FIG. 13B shows a representation of simulations (labeled Scenario 2) in which the second difference (from Equation 1) was computed 100 times at each time step as the electrode position was incrementally varied over the length of the channel. The peak second difference and electrode position corresponding to the peak were stored in temporary variables. In both Scenario 1 (FIG. 13A) and Scenario 2, after the AP had been advanced entirely through the channel extents, the second difference peaks recorded at each time step were compared to yield a maximum second difference. In scenario 2 simulations, the electrode position corresponding to the maximum second difference served as an additional output variable.

Signals obtained when the electrode was fixed at center or when it was permitted to find its optimum location were compared for the different AP waveforms and channel lengths. Because many nerve bundles contain both afferent and efferent fibers firing asynchronously within the nerve, the $2^{nd}$ Difference was computed for APs traveling opposite to the direction for which the optimum electrode position was found. It was expected that an offset that had been optimized for recording an AP traveling in one direction would significantly attenuate the same AP traveling in the opposite direction through the channel. This is a useful feature with practical implications because it can inform the design of channels able to easily discriminate between afferent and efferent activity in the captured nerve. A sensitivity analysis was performed, which varied the spatial extent of each AP in channels using the optimum offset to determine the extent to which a recording advantage remained robust to variations in the waveform for which the ideal offset had been designed to record optimally.

Figure 14:
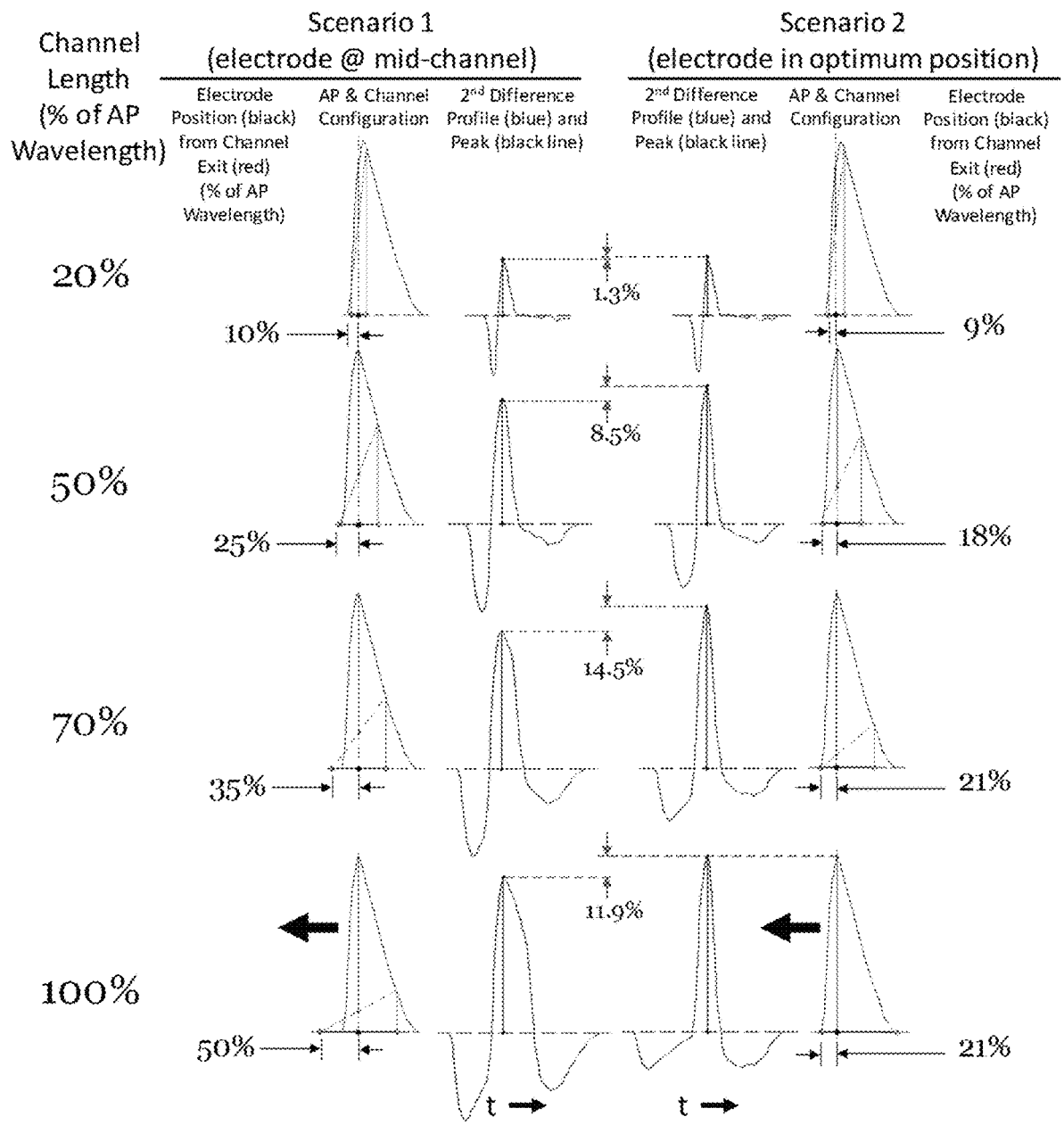
FIG. 14 shows AP waveforms for the two Scenarios discussed for FIGS. 13A and 13B, at different channel lengths. The maximum second difference amplitudes (vertical line) in each waveform are enhanced when the electrode is positioned nearer the channel exit (left-most (red) dot in each waveform plot) compared to when the electrode is fixed at mid-channel. For short channels, the difference in signal amplitudes in each scenario is small (e.g., only 1.3% of the AP peak at channel lengths of 20% of the AP wavelength). For longer channel lengths, these differences become more pronounced (e.g., 14.5% of the AP peak at a channel length of 70% of the AP wavelength). When channel length is equal to 100% of the wavelength, an offset of 21% results in a maximum second difference equal to the AP peak, whereas the centered configuration yields a second difference amplitude that is less than this by 11.9% of the AP peak. Dashed (red) horizontal lines provided at the maximum of each second difference profile highlight amplitude differences between output waveforms. The "AP & Channel Configuration" columns depict the moment in time when the electrode (middle dot) and AP are aligned to yield the maximum second difference (vertical line), which generally occurs when the AP peak is coincident with the electrode (X-axis is distance). The diagonal line connecting the AP potential at the channel ends enables the second difference along the channel to be readily visualized. Solid horizontal lines at the base of each AP waveform represent the channel extents with entrance and exit denoted by right-most (green) and left-most (red) dots, respectively. The "2nd Difference Profile and Peak" column shows the shape of the second difference in time as the AP is stepped through the channel (X-axis is time as indicated in the bottom row). All AP waveforms travel from right to left through their channel, as indicated by the black arrows pointing to the left in the bottom row of FIG. 14.

FIG. 14 shows AP waveforms for the two Scenarios discussed for FIGS. 13A and 13B, at different channel lengths. The maximum second difference amplitudes (vertical line) in each waveform are enhanced when the electrode is positioned nearer the channel exit (left-most (red) dot in each waveform plot) compared to when the electrode is fixed at mid-channel. For short channels, the difference in signal amplitudes in each scenario is small (e.g., only 1.3% of the AP peak at channel lengths of 20% of the AP wavelength). For longer channel lengths, these differences become more pronounced (e.g., 14.5% of the AP peak at a channel length of 70% of the AP wavelength). When channel length is equal to 100% of the wavelength, an offset of 21% results in a maximum second difference equal to the AP peak, whereas the centered configuration yields a second difference amplitude that is less than this by 11.9% of the AP peak. Dashed (red) horizontal lines provided at the maximum of each second difference profile highlight amplitude differences between output waveforms. The "AP & Channel Configuration" columns depict the moment in time when the electrode (middle dot) and AP are aligned to yield the maximum second difference (vertical line), which generally occurs when the AP peak is coincident with the electrode (X-axis is distance). The diagonal line connecting the AP potential at the channel ends enables the second difference along the channel to be readily visualized. Solid horizontal lines at the base of each AP waveform represent the channel extents with entrance and exit denoted by right-most (green) and left-most (red) dots, respectively. The "2nd Difference Profile and Peak" column shows the shape of the second difference in time as the AP is stepped through the channel (X-axis is time as indicated in the bottom row). All AP waveforms travel from right to left through their channel, as indicated by the black arrows pointing to the left in the bottom row of FIG. 14.

FIG. 14 presents the $2^{nd}$ Difference profiles generated when the M&L action potential is simulated as traveling from right to left through each of four different channel lengths: 20, 50, 70 and 100% of AP wavelength. For each channel length, the peak of the output waveform corresponding to Scenario 1, the condition when the electrode is fixed at mid-channel, is compared to the waveform generated under Scenario 2, where the electrode was permitted to find a position which resulted in the largest 2nd Difference peak amplitude. The relative position of the AP in the channel corresponding to the moment when the peak 2nd Difference is reached for each scenario is also shown.

At a channel length of 20% of AP wavelength, the optimum position of the electrode was found to occur at 9% of the AP wavelength, nearly equivalent to the mid-channel position at 10% of the AP wavelength, with the maximum $2^{nd}$ Differences waveforms differing only by 1.3% of the AP peak. However, at longer channel lengths, signal amplitudes diverged in favor of an off-centered electrode configuration. At channel lengths of 70% AP wavelength, the output signal for the off-centered configuration exceeded the centered one by almost 15% of the AP peak. When channel length equals the AP wavelength, the off-centered configuration yielded the maximum recorded signal possible (i.e., maximum $2^{nd}$ Difference equals 100% of the AP peak), whereas the centered configuration yielded an output signal that is less than the maximum possible by more than 10% (i.e., 11.9%) of the AP peak.

At longer channel lengths, FIG. 14 also demonstrates that the optimum electrode position, measured as the electrode's distance from the channel exit, remains constant and equals the spatial extent of the AP's rising phase. As shown in FIGS. 12A-12D, the rising phase of the M&L AP is 21% of its wavelength, which is was also found to be the optimum offset distance for the electrode from the channel exit for channel lengths of 70% of the AP wavelength or greater. This result can be proven to be universally true if APs are modeled as triangular waveforms.

Figure 15A:
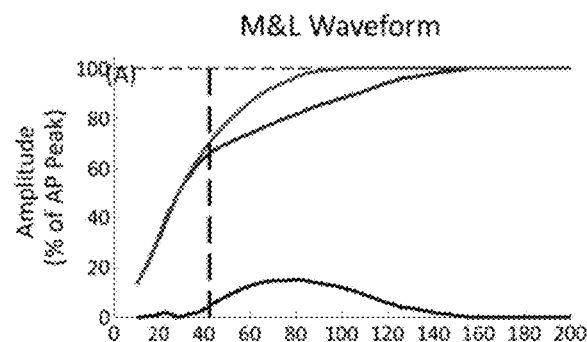
FIGS. 15A-15D show maximum second difference amplitudes plotted against channel length for centered (lower (blue) line in the upper section of each plot) and optimum, off-center (upper (red) line in the upper section of each plot) electrode configurations.
Figure 15B:
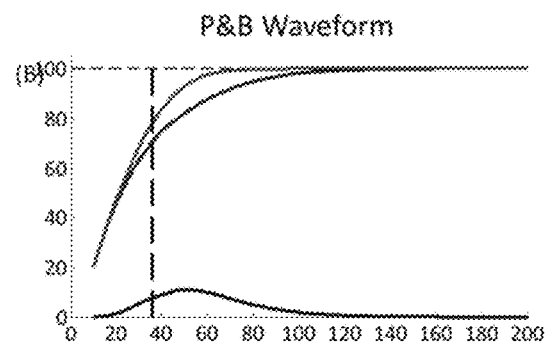
Figure 15C:
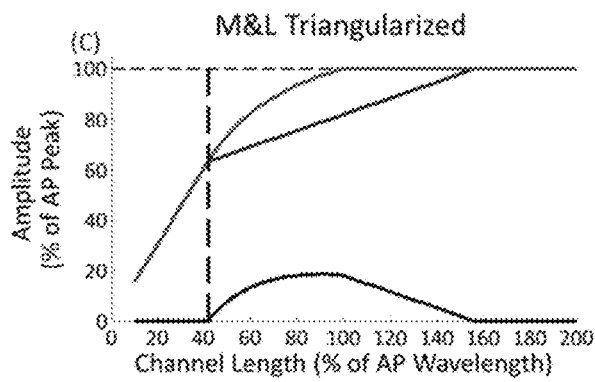
Figure 15D:
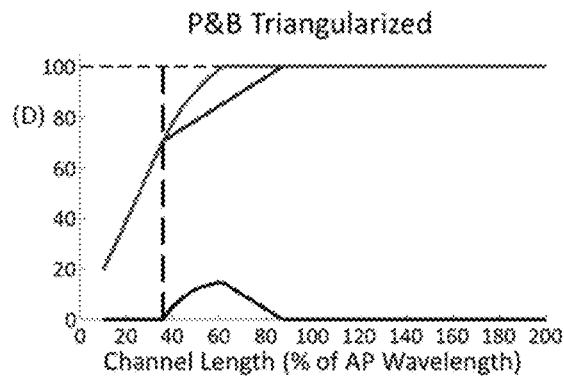

FIGS. 15A-15D show maximum second difference amplitudes plotted against channel length for centered (lower (blue) line in the upper section of each plot) and optimum, off-center (upper (red) line in the upper section of each plot) electrode configurations. FIG. 15A is for an M&L waveform; FIG. 15B is for a P&B waveform; FIG. 15C is for a triangularized representation of the M&L waveform of FIG. 15A; and FIG. 15D is for a triangularized representation of the P&B waveform of FIG. 15B. For channel length of less than twice the spatial spread of the AP's rising phase (vertical dashed line), the signal amplitudes were nearly equivalent, implying that the optimum electrode is at mid-channel. When channel lengths exceed twice the rising phase of the AP (42% for the M&L waveforms and 36% for the P&B waveforms), the optimum electrode position is offset from mid-channel, a configuration that results in greater signal amplitudes over a wide range of channel lengths compared to the centered electrode configuration. The point of divergence is seen to be exact in the triangularized AP representations (FIGS. 15C and 15D), a result that can be demonstrated mathematically. Differences in signal amplitude between the optimum and centered configurations (lower-most line in each plot) peak at about 80% of the M&L wavelength and 50% of the P&B wavelength.

FIGS. 15A-15D summarize the results shown in FIG. 14. For each AP waveform, there is a range of channel lengths over which the optimal electrode position is different than the mid-channel position and yields greater signal amplitudes. Signal amplitudes begin to diverge when channel lengths exceed twice the spatial extent of the rising phase of the AP, indicated by the vertical dashed lines in FIGS. 15A-15D. This point of divergence is exact for the idealized triangularized waveforms (FIGS. 15C and 15D), a result that can be demonstrated mathematically. The offset configuration results in greater signal amplitudes compared to the centered configuration for channels ranging in length from 42% to about 150% of the AP wavelength for the M&L waveform and 36% to about 100% of the wavelength for the P&B waveform. Differences in signal amplitude between the centered and optimum, off-centered, electrode configuration are as high as 15% for channel lengths of about 80% of the M&L wavelength (FIG. 15A). The P&B (FIG. 15B) waveform presents with similar trends, with differences in signal amplitude exceeding 10% at a channel length of approximately 50% of the P&B wavelength. Differences in signal amplitude between the centered and optimum are seen to be greater for the more asymmetrical M&L waveforms and persist over a greater range of channel lengths compared to the more symmetrical P&B waveforms (FIG. 15A vs 15B and 15C vs 15D).

Figure 16A:
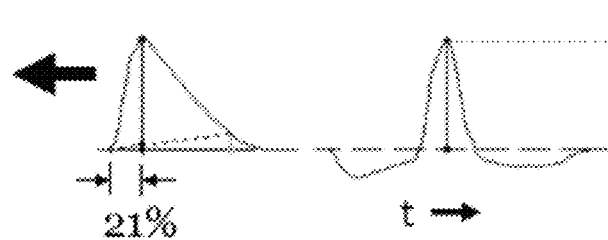
FIGS. 16A and 16B show simulated waveforms for normal AP propagation (FIG. 16A) and reverse AP propagation (FIG. 16B), demonstrating that an off-centered electrode configuration can discriminate between afferent and efferent neural activity.
Figure 16B:
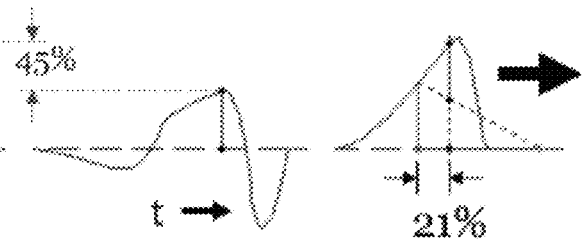
Figure 17A:
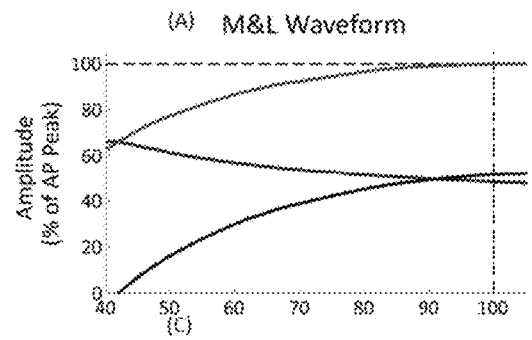
FIGS. 17A-17D show maximum second difference amplitudes plotted against channel length for APs of equivalent shape and magnitude traveling in the preferred right to left direction (higher (red) line in each plot) and the opposite direction ((blue) line that is in the middle vertically at the lateral middle section of each plot) through the channel. The line that is the lowest at the left side of each plot is for the difference in amplitude between the right to left direction and the opposite direction in each plot.
Figure 17B:
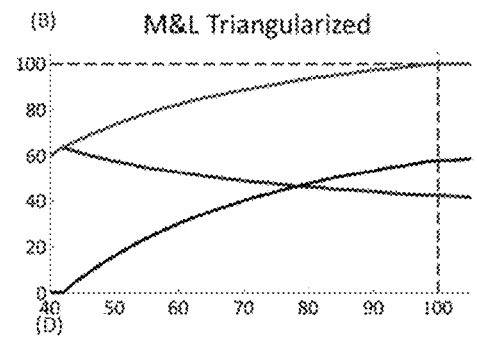
Figure 17C:
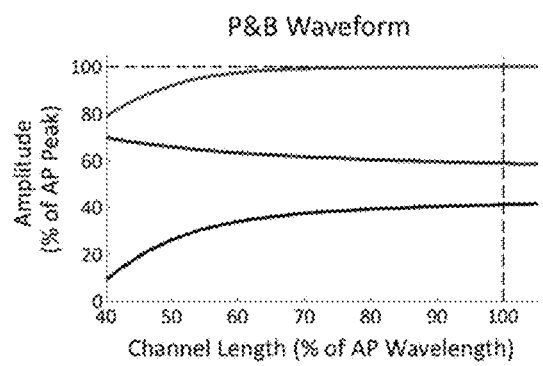
Figure 17D:
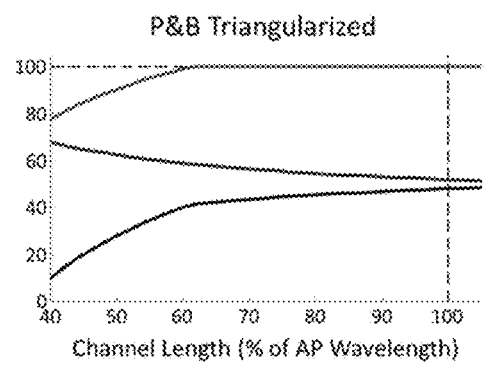

The off-centered electrode configuration attenuates APs traveling in a direction opposite to the one the offset was designed to target. FIGS. 16A and 16B present the 2nd Difference profiles (in time) generated when the M&L waveform travels in opposite directions through a channel having a length of 80% of the AP wavelength and a recording electrode situated at 21% from the channel exit. This position was previously determined to be the optimum electrode position for this channel length for the M&L waveform propagating in the preferred, or "normal", direction from right to left through the channel. While the offset configuration is ideally suited to record the M&L waveform propagating from right to left, it is a comparatively poor configuration for recording the same waveform traveling from left to right in the opposite, or "reverse", direction, there being a difference of 45% between the maximum 2nd Difference amplitudes for each case.

FIGS. 17A-17D extend these results to include all simulated waveforms and channels longer than 40% of the AP wavelength, which, being approximately twice the spatial spread of the M&L and P&B wavelengths, is the minimum length for which the offset configuration provides a recording advantage. The optimum offsets previously determined of 21% and 18% of the AP wavelength were used for the M&L and P&B waveforms, respectively. As channel length was increased, the offset configuration resulted in a progressive attenuation of the output signal for APs travelling in the "reverse" direction. Those traveling in the preferred direction were enhanced. For example, at a channel length equal to 100% of the AP wavelength, the output signal for the M&L waveform was attenuated to below 50% of the AP peak for "reverse" propagation, representing a considerable reduction in the recorded signal compared to the forward propagating waveform where the 2nd Difference reaches its maximum value of 100% of the AP peak. Signal amplitudes flatten out and approach constant values as channel lengths approach the AP wavelength, which suggests channel lengths longer than one AP wavelength does not buy additional discriminating ability. The P&B waveforms demonstrated similar trends, except that recording advantages began to plateau sooner than the M&L waveform at channel lengths of around 70-80% of their AP wavelengths.

Figure 18A:
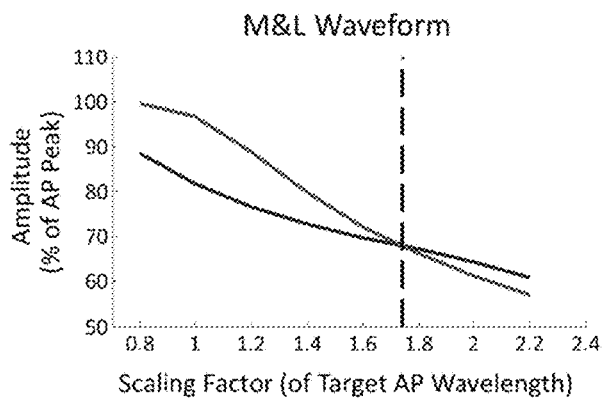
FIGS. 18A and 18B show maximum second difference amplitudes plotted against target AP wavelength for centered (the (blue) line that is lower at the left side of each plot) and off-center, optimum (the (red) line that is higher at the left side of each plot) electrode configurations.
Figure 18B:
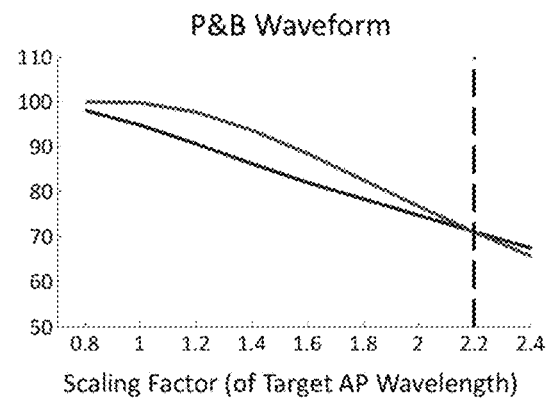

FIGS. 18A and 18B show maximum second difference amplitudes plotted against target AP wavelength for centered (the (blue) line that is lower at the left side of each plot) and off-center, optimum (the (red) line that is higher at the left side of each plot) electrode configurations. FIG. 18A is for an M&L waveform, and FIG. 18B is for a P&B waveform. For the optimum electrode configuration, the electrode was located at 21% of the M&L wavelength and 18% of the P&B wavelength from the channel exit. Actual target action potentials would need to exceed those used to optimize the electrode position by more than 1.7 times the M&L wavelength and 2.2 times P&B wavelength (dashed vertical lines in FIGS. 18A and 18B, respectively) before this ideal offset configuration would perform worse than the centered design.

Because the optimum position for an offset electrode configuration is a function of AP wavelength in situations where channels are sufficiently long, the question of how much variation in target AP wavelength would an offset configuration tolerate before it loses its recording advantage over the centered electrode configuration was addressed. FIGS. 18A and 18B shows the impact of varying the target AP wavelength on the amplitude of recorded signals for the centered and off-centered electrode configurations. All output signals were computed using a channel length of 80% of the wavelength of the original AP waveforms shown in FIGS. 12A-12D. With the electrode positioned at its optimum location of 21% from the channel exit for the M&L waveform, the AP wavelength would need to be approximately 1.7 times longer before the offset configuration gives the same output amplitude as the centered approach (see dashed vertical line at the intersection of the output amplitudes for each electrode configuration). When the electrode is positioned at its ideal offset of 18% from the channel exit for the P&B waveform, the recorded AP wavelength would need to be more than twice that of the original AP wavelength before the offset configuration failed to result in greater output signals compared to those obtained using the centered electrode configuration. These results suggest the offset configuration is reasonably robust to variations in the wavelength of the target AP upon which the optimum offset position was originally based.

Figure 19:
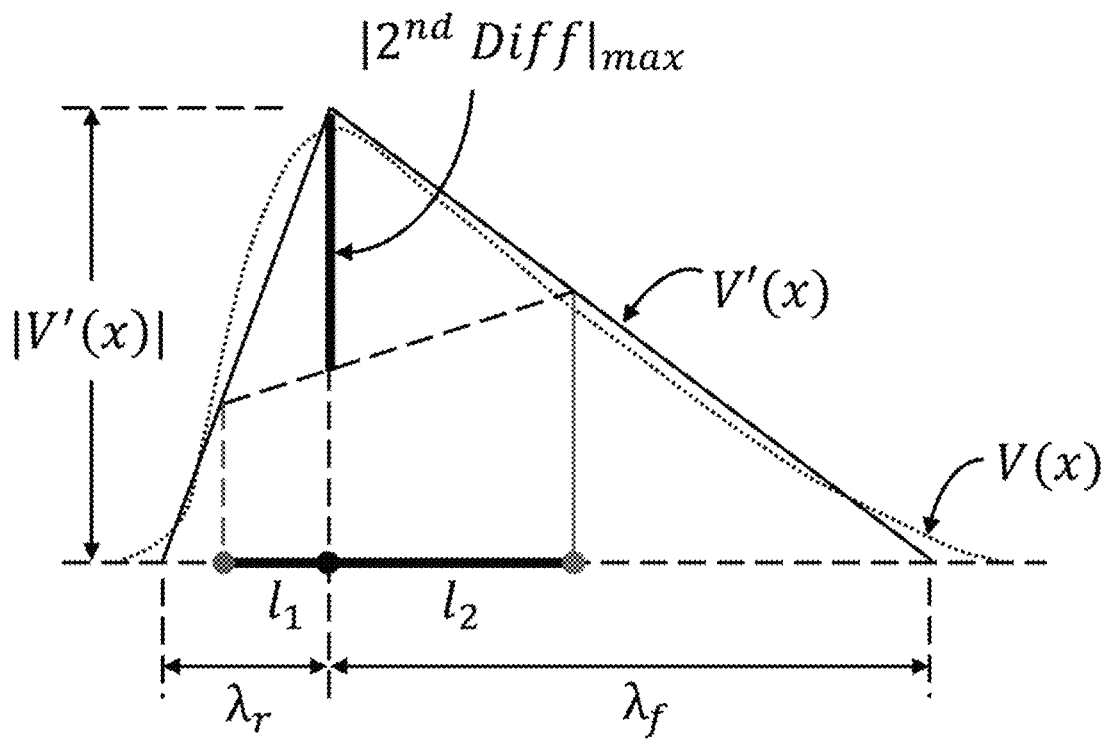
FIG. 19 shows an AP waveform, demonstrating that the maximum second difference, |2nd Diff|max, can be calculated for any channel length and electrode position if the AP waveform, V(x), is approximated by a triangular waveform, V'(x). In this case, the only parameters that are needed to estimate the maximum amplitude of the recorded extracellular signal are the amplitude of the peak of the triangular approximation, |V'(x)|, the spatial extents of the rising and falling phases of the triangular approximation ($\lambda r$ and $\lambda f$), and the distance from the electrode (middle dot) to the channel exit (left (red) dot) and entrance (right (green) dot), $l_1$ and $l_2$, respectively.

Using a triangular approximation of the spatial profile of a given AP waveform the maximum $2^{nd}$ Difference amplitude may be calculated for any given channel length and electrode position. This is possible because the $2^{nd}$ Difference term reaches its maximum at one instant in time as the AP passes through the channel, namely, when the peak of the triangularized AP is coincident with the electrode. While this fact may be proven mathematically, it is readily appreciated by noting any vertical line drawn between the triangular approximation of the AP, V'(x), and the dashed diagonal line in FIG. 19 must always be shorter than the one drawn at vertex of V'(x), depicted as the bold vertical line in FIG. 19.

Using only 5 parameters, Equation 2 below may be used to estimate the maximum $2^{nd}$ Difference for situations where the channel length does not exceed the AP wavelength and the distance from the electrode to the channel exit does not exceed the rising phase of the AP:

$$|2^{nd}\ Diff|_{max} = |V'(x)| \cdot \frac{l_1 l_2}{l_1 + l_2} \cdot \frac{\lambda_r + \lambda_f}{\lambda_r \lambda_f} \qquad (2)$$

This is believed to be the first time an analytical expression for the $2^{nd}$ Difference term has been provided. It worth noting the relative independence of Equation 2 on actual length units, because the product of the ratios containing the spatial terms results in a cancellation of units. An easy validation of Equation 2 is to use it to estimate the $2^{nd}$ Difference amplitude for the situation depicted in FIG. 11B, where the AP wavelength is completely contained within the channel and the AP peak is coincident with the recording electrode. In this case, $l_1=\lambda_r$ and $l_2=\lambda_f$. Making these substitutions into Equation 2 yields |V'(x)| as the amplitude of the peak $2^{nd}$ Difference, as expected.

Figure 20:
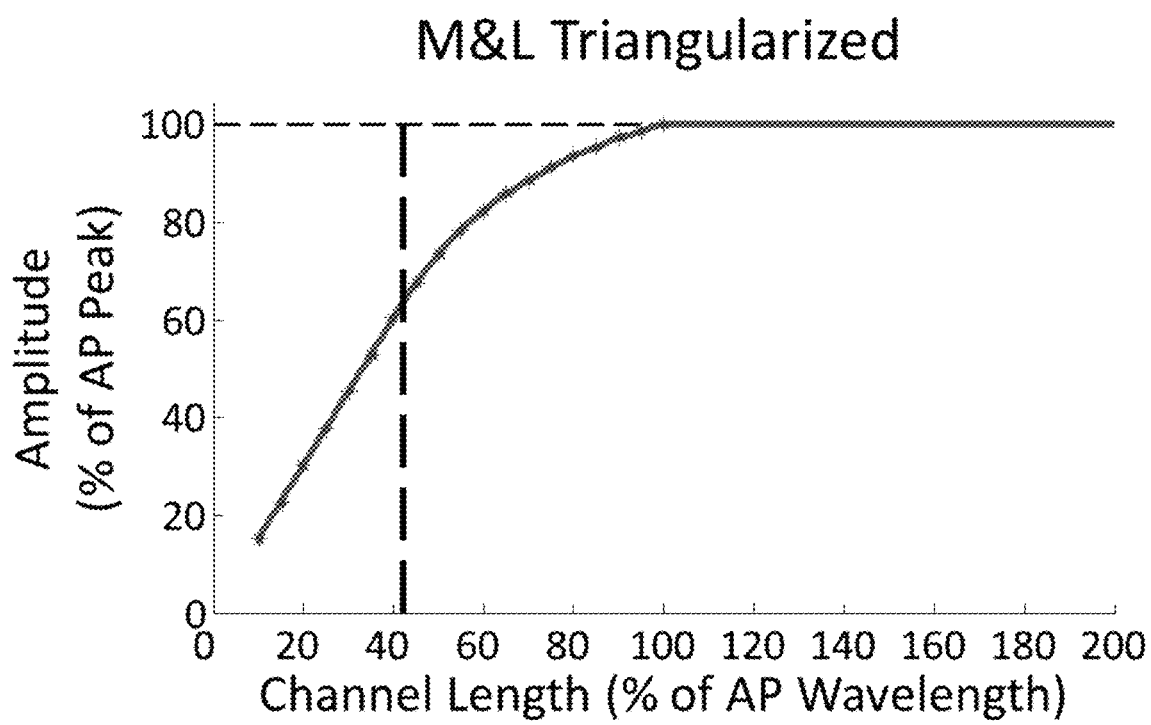
FIG. 20 shows an M&L triangularized plot of amplitude (as a % of AP peak) versus channel length (as a % of AP wavelength). The (red) line is identical to that in FIG. 15C, which equals the maximum second difference amplitude for the M&L triangularized waveform under Scenario 2 for different channel lengths. The (blue) asterisks are the maximum second difference amplitudes computed using Equation 2 and give identical results, as expected.
Figure 21A:
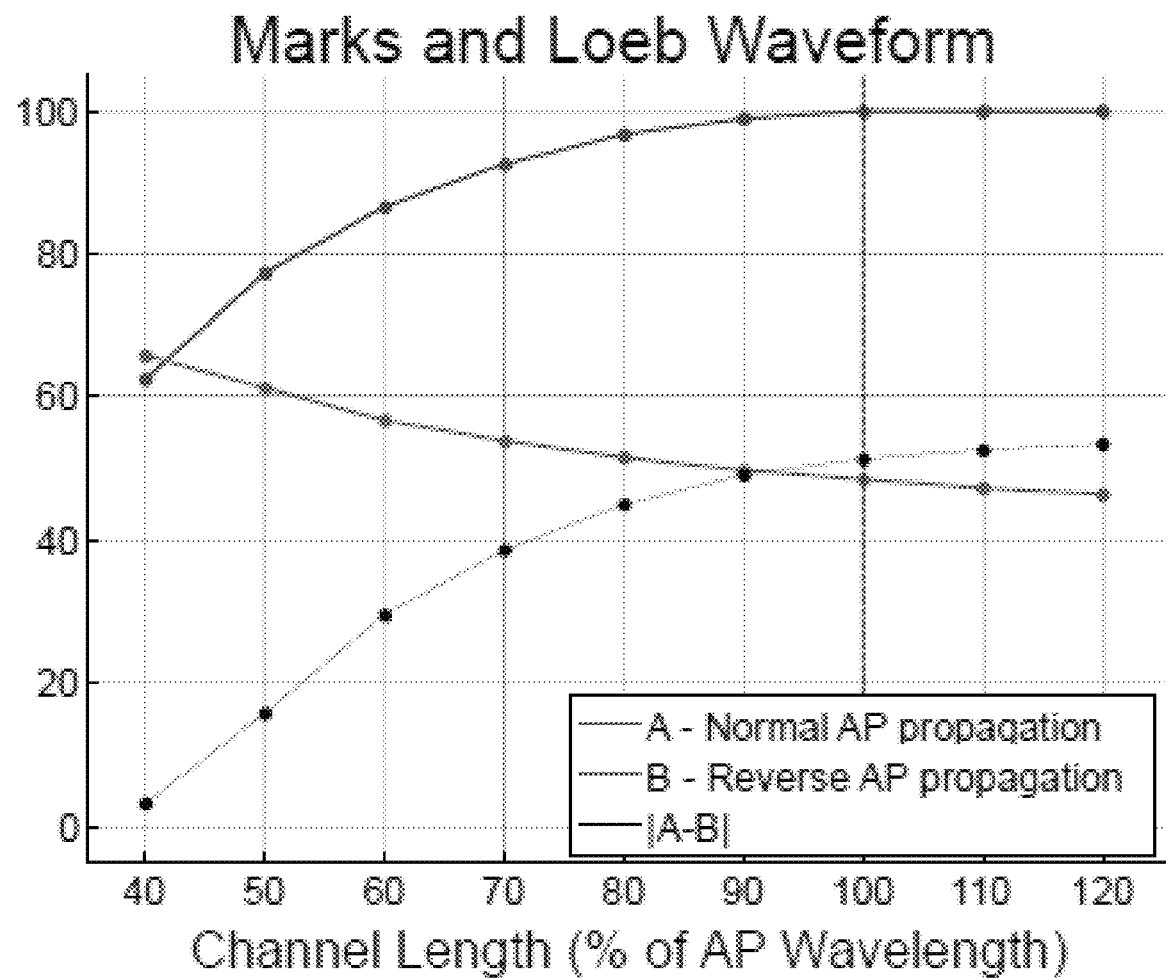
FIG. 21A shows an enlarged version of FIG. 17A.
Figure 21B:
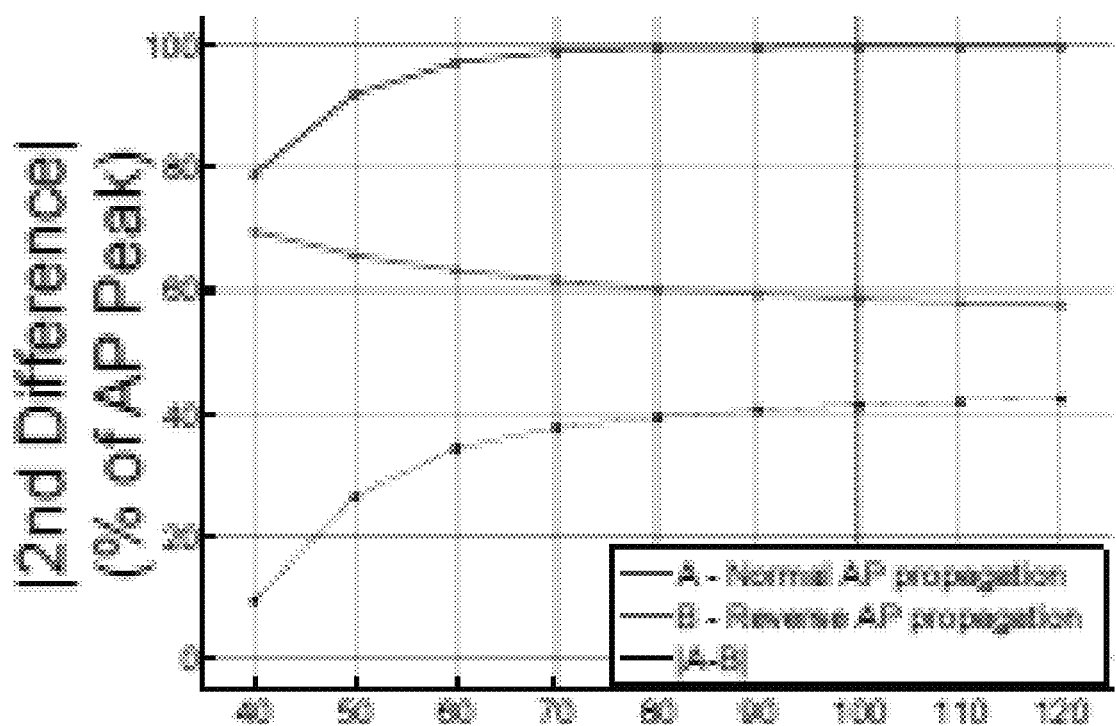
FIG. 21B shows an enlarged version of FIG. 17C.
Figure 21C:
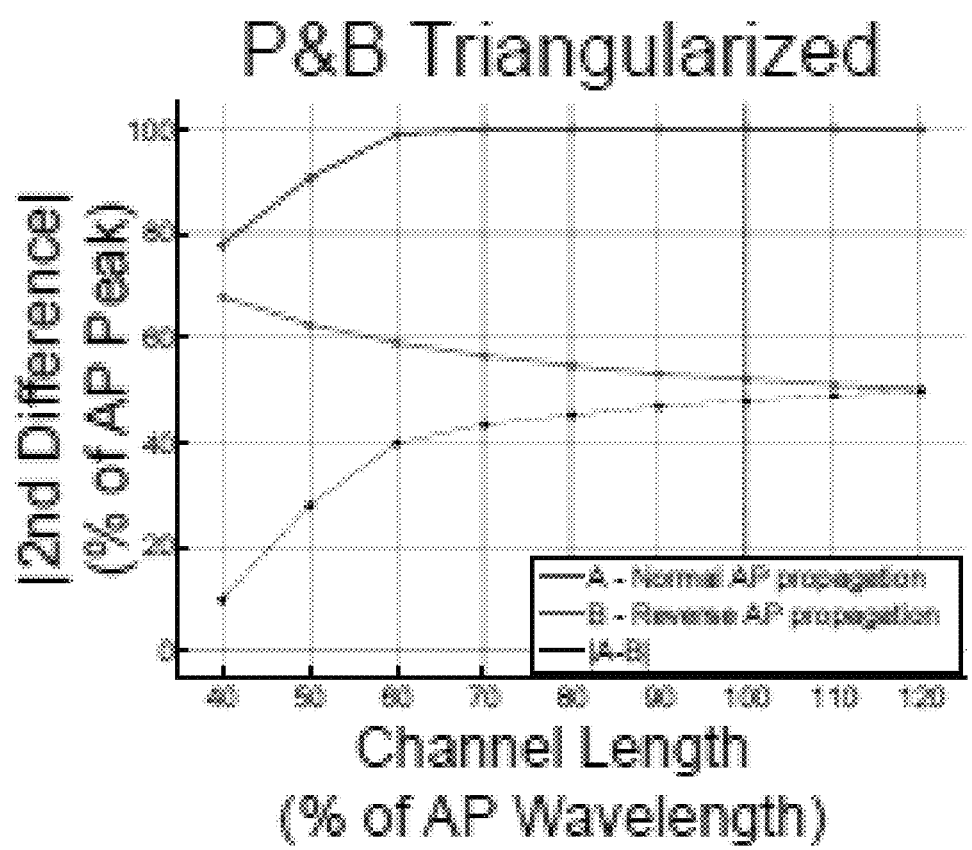
FIG. 21C shows an enlarged version of FIG. 17D.
Figure 22A:
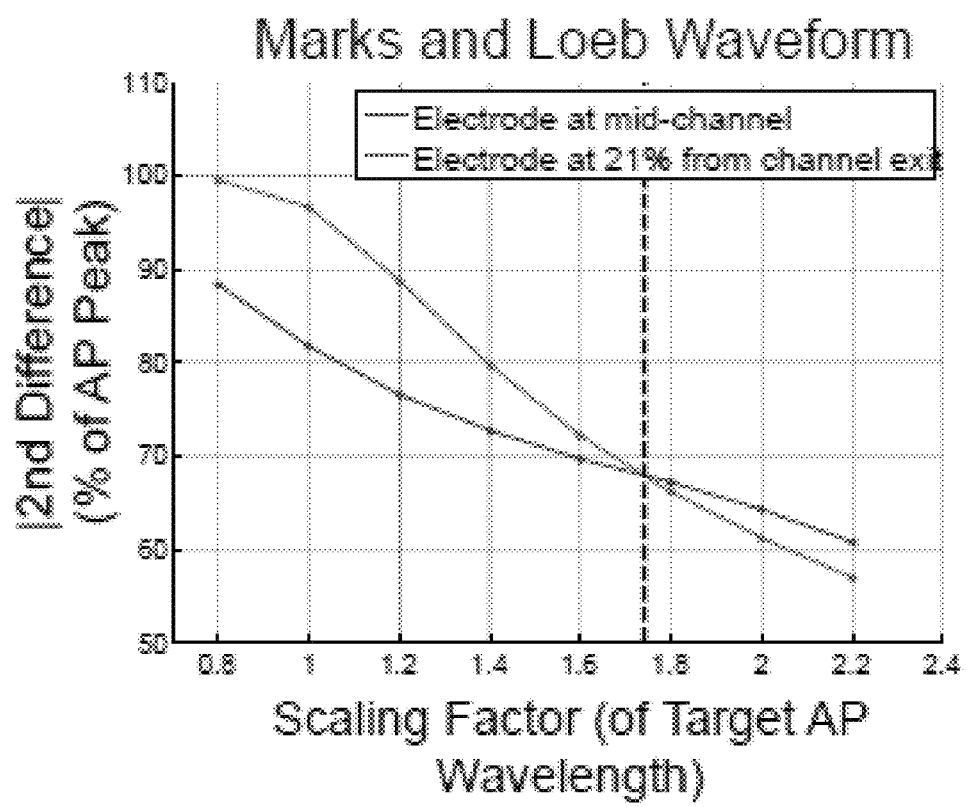
FIG. 22A shows an enlarged version of FIG. 18A.
Figure 22B:
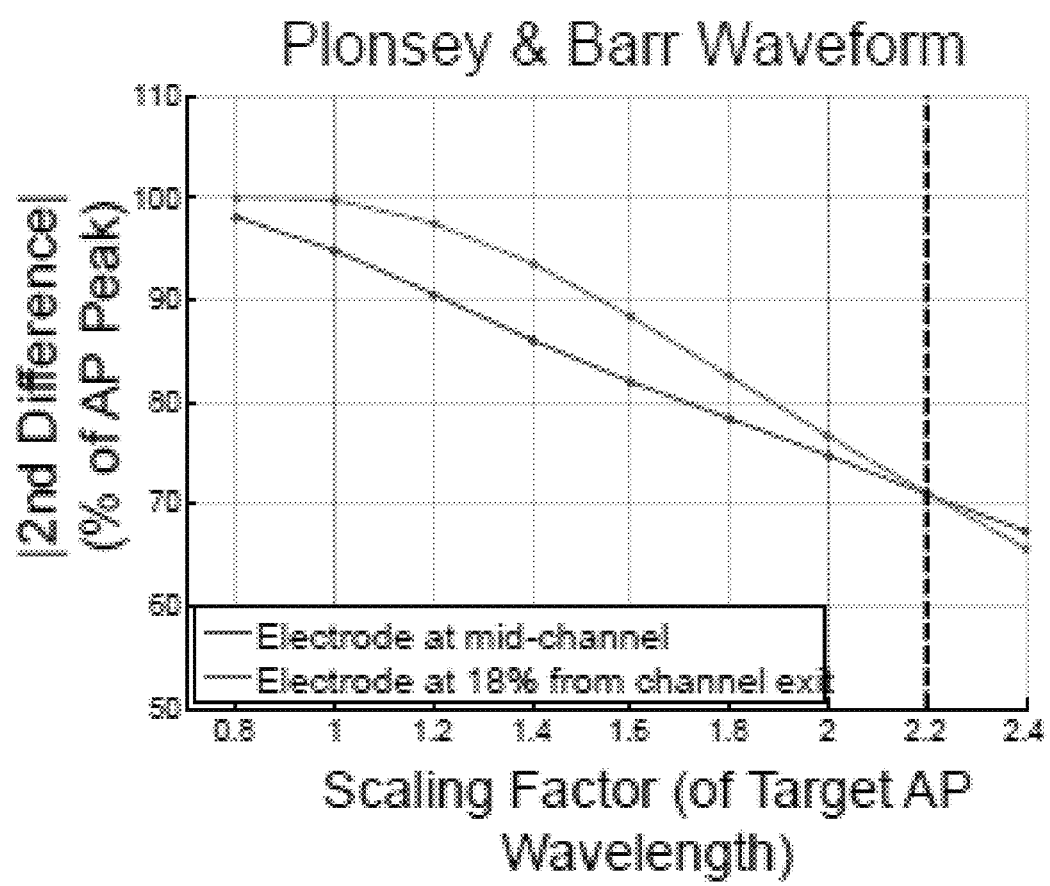
FIG. 22B shows an enlarged version of FIG. 18B.

FIG. 20 illustrates the use of Equation 2 to predict the maximum $2^{nd}$ Difference amplitude as a function of channel length of the M&L triangularized waveform, where |V'(x)|=100% and $\lambda_r$=21% ($\lambda_f$=79%). The distance from the electrode to the channel exit equals half the channel length for channels less than 42% (twice the spatial extent of the rising phase of the AP) and 21% for channel lengths greater than this. As expected, the results are identical to those depicted in FIG. 15C for the M&L triangularized waveform under Scenario 2, where the electrode was permitted to find its optimum position. Thus, for APs that may be adequately modeled as triangular waveforms, Equation 2 may be used in lieu of simulations to compute the maximum $2^{nd}$ Difference for any channel configuration, insofar as the channel length is less than the AP wavelength and the distance of the electrode to the channel exit does not exceed the spatial extent of the rising phase of the AP. The authors note that expressions like Equation 2 may be derived for channels longer than the AP wavelength and/or cases where the distance of the electrode to the channel exit is greater than the spatial extent of the APs rising phase, and the reader is encouraged to do so.

Temporal, rather than spatial parameters, are frequently used to characterize action potentials. Doing so enables the impact of action potential velocity on the amplitude of extracellular recordings to be appreciated. Any spatial parameter of the action potential may be gotten by multiplying its corresponding temporal analog by the speed of AP propagation, C. Thus, $$\lambda_r = C \cdot \tau_r \quad (3)$$

$$\lambda_f = C \cdot \tau_f \quad (4)$$

Substituting these expressions for $\lambda_r$ and $\lambda_f$ into Equation 2 and noting that the peak amplitude of the triangularization of the AP in space and time are equivalent (i.e., $|V'(x)|=|V'(t)|$), enables Equation 2 to be rewritten as:

$$|2^{nd}\ Diff|_{max} = \frac{|V'(t)|}{C} \cdot \frac{l_1 l_2}{l_1 + l_2} \cdot \frac{\tau_r + \tau_f}{\tau_r \tau_f} \quad (5)$$

Equation 5 may be used to estimate the maximum $2^{nd}$ Difference amplitude for a triangularized action potential traveling at conduction speed C through a channel of length, $l_1+l_2$, where the recording electrode is situated at a distance $l_1$ from the channel exit. Like Equation 2, Equation 5 is restricted to situations where channel length ($l_1+l_2$) does not exceed the AP wavelength, given by the product of C and the AP duration ($\tau_r+\tau_r$), and the distance from the electrode to the channel exit ($l_1$ does not exceed the rising phase of the AP, given by the product of C and $\tau_r$.

For two action potentials having equivalent temporal profiles (i.e., V(t) and V'(t) is the same for both), Equation 5 shows that a channel designed to maximize the $2^{nd}$ Difference amplitude obtained for one AP propagating at a speed C would need to be doubled in length to maximize the $2^{nd}$ Difference for another travelling at twice this velocity, or 2 C. Thus, longer channel lengths are required to optimize the $2^{nd}$ Difference amplitude for faster conducting APs. This does not necessarily mean shorter channels would yield inadequate signals for high-velocity APs since the $$-\frac{R_e}{R_i}$$

leading term in Equation 1 is likely to be larger for large diameter fast-conducting fibers compared to smaller diameter fibers conducting at slower velocities, which would tend to offset the reduced $2^{nd}$ Difference amplitudes obtained for the fast-conducting fibers.

If action potential waveforms were symmetrical about their peaks the mid-channel electrode placement would always be the ideal electrode position for pseudo-tripolar electrode configurations. This situation would occur if $\lambda_r$ were equal to $\lambda_f$. It is apparent from Equation 2 in this case that the maximum $2^{nd}$ Difference is obtained then when $l_1=l_2$; in other words, the electrode is best situated at mid-channel. However, because it takes potassium ions about three to four times longer to exit the axoplasm than it does for sodium to enter initially, APs are asymmetrical waveforms in time and, therefore, in space as well. It is this inherent asymmetry of APs that lies at the core of this analysis and any recording advantage that is achieved by asymmetric placement of the recording electrode in recording devices (e.g., in pseudo-tripolar electrode designs). This analysis is believed to be the first to use Equation 1 to systematically vary the electrode position as a function of channel length to explore the implications of using an offset electrode configuration to enhance neural recordings and improve electrode design.

The peripheral nervous system of mice contains approximately three times as many afferent axons as efferent ones, an anatomical fact that likely holds across most, if not all mammalian nervous systems. This overwhelming and disproportionate dedication of neural resources in favor of sensation suggests an underlying principle of mammalian nervous systems, namely, that motor systems that lack extensive and nuanced sensory feedback are inferior to those that do. The fact that many human upper-extremity amputees cite lack of sensory feedback as a primary reason for prosthesis rejection would support this view. Because most peripheral nerves are mixed nerves, containing thousands of afferent and efferent fibers transmitting action potentials simultaneously in both directions, it is crucial that technologies developed for neural recording can preferentially detect signals traveling in one direction over those travelling in the opposite direction. While bipolar electrode configurations are the simplest approach for doing this, compared to the pseudo-tripolar configuration they do not perform as well in chronic settings where EMG artifact can easily eclipse recorded neural activity.

Pseudo-tripolar electrode configurations with non-centrally placed recording electrodes are inherently capable of discriminating between action potentials traveling in opposite directions in the nerve. This feature leads to cuffs and channels (e.g., microchannels) outfitted with at least two circumferential recording sites, where the left-most electrode is optimally positioned to record a target AP waveform traveling from the right to the left and the right-most electrode is optimally positioned to record another target AP waveform traveling from the left to the right. If these two target waveforms had similar temporal parameters and speed, the offset of each electrode from the ends of the cuff would be equivalent. One use for this type of design is to distinguish proprioceptive feedback from motor commands in a mixed nerve. Such a design can be, for example, used in closed-loop functional electrical stimulation (FES) systems to assist individuals with a partial spinal cord injury who have retained the ability to issue weak motor commands. An offset pseudo-tripole electrode design could detect motor intent at one electrode and the state of muscle stretch through proprioceptive activity detected at the other. The motor intent signal can be used to appropriately time artificial muscle stimulation, which can be appropriately modulated by the recorded proprioceptive signals. The offset design of embodiments of the subject invention can achieve good results using a cuff or channel that is not excessively long and without the need to perform any real-time computations.

To design a channel for neural recording, one place to start is with the speed of the AP to be recorded, because the speed determines the spatial profile of the AP along the axon. The rising phase of the target AP potential is especially important because it dictates where to place the recording electrode. For channels shorter than twice the spatial spread of the rising phase of the target AP, the ideal electrode placement would be at mid-channel (see maximum $2^{nd}$ Difference amplitudes for channel lengths to the left of the dashed vertical lines in FIGS. 15A-15D). When channel lengths exceed this transition length, recording amplitudes are maximized by placing the recording electrode a fixed distance, equal to the spatial spread of the APs rising phase, from the channel exit. This remains true for channels up to and beyond one AP wavelength.

Table 1 below gives offset dimensions for a slow (16 m/s) and a fast (64 m/s) AP recorded by Paintal from the vagus and saphenous nerves in cats (Paintal, 1966).

TABLE 1

| Speed[1] (m/s) | Rise time[1] (ms) | Fall time[1] (ms) | Duration[1] (ms) | Spatial spread of the AP's rising phase (ideal offset distance, measured from channel exit) (mm) | Transition channel length (mm) |
|---|---|---|---|---|---|
| C | $\tau_r$ | $\tau_f$ | $\tau_d$ | $\lambda_r$ ($=C \times \tau_r$) | $L_{transition}$ ($=2\lambda_r$) |
| 16 | 0.13 | 0.35 | 0.48 | 2.1 | 4.2 |
| 64 | 0.10 | 0.26 | 0.36 | 6.4 | 12.8 |

[1]Action potential (AP) speed and temporal data taken from Paintal AP (1966) for cat An electrode placed 2.1 mm from the channel exit for all channels longer than a transition length of 4.2 mm would be the optimum electrode position for recording the 16 m/s AP with temporal characteristics shown. Similarly, a 64 m/s AP would optimally be recorded using channel lengths greater than 12.8 mm and a recording electrode located a distance of 6.4 mm from the channel's exit. For channels shorter than these transition lengths, a mid-channel electrode placement would be optimal. Using the ideal offset of 7.7 and 23 mm for the slow and fast fibers, respectively, maximum signal amplitudes would be achieved at channel lengths equal to one AP wavelength. This would not be the case for the centered configuration, where signal amplitudes would be between 10-15% less than their maximum value at channel lengths equal to 100% of the AP wavelength (see FIGS. 15A-15D). Thus, the offset configuration affords an opportunity to record the maximum signal possible using the shortest channel length possible (i.e., equal to one AP wavelength.)

Paintal showed rise times remain relatively constant at about 0.1 ms over a wide range of AP speeds. For design purposes, a simple rule of thumb for estimating the ideal distance of the electrode from the channel exit (in millimeters) would simply be to divide the speed of the target AP (in m/s) speed by 10. The fall time can be computed from knowledge of the APs duration. Using these parameters, Equation 5 may be used to estimate the maximum signal amplitudes that could be expect to be recorded.

The optimal electrode position is measured with respect to the channel's exit, not its center. Once a target waveform has been identified, the optimal distance from the channel exit remains constant for all channel lengths exceeding the transition length, since the spatial spread of the rising phase is a constant for a given target AP waveform.

Balanced pseudo-tripole electrodes configurations, with the recording electrode situated at mid-channel, are sometimes used because this approach provides good rejection of large EMG signals external to the implant (R. B. Stein et al., 1975). However, most pseudo-tripolar electrodes are not truly "balanced" (Hoffer & Kallesoe, 2001). This may be due to the recording electrode not being exactly centered between the shorted end contacts (i.e., reference terminal) or, if it is, then the lumped resistance of the extracellular fluid from one end of the channel to the recording electrode may be different than what is from the other end to the recording electrode. In either case, an external voltage source, from EMG for example, can produce a potential at the reference terminal that is different than the potential at the recording electrode, resulting in imperfect cancellation of this unwanted signal, or noise.

Dual-cuff electrodes, where an external reference is sandwiched between the outside of the cuff and another larger cuff that surrounds the first, can provide excellent noise cancellation (e.g., in imperfectly balanced pseudo-tripolar configurations). The thermal, or Johnson, noise would theoretically be reduced using an offset configuration compared to the traditional balanced approach. This is because the Johnson noise is proportional to the square root of the resistance path from the recording electrode to the end terminals. This resistance path, which equals the resistance from each end contact to the recording electrode taken in parallel, is maximum when the electrode is located mid-channel and becomes reduced as the electrode is moved towards either end. Also, even if the common-mode rejection capability were to potentially be compromised due to impedance mismatching issues inherent in the unbalanced, offset configurations, their ability to discriminate between APs traveling in opposite directions is preserved, insofar as the noise from external EMG is smaller than the largest detected neural signal.

The results demonstrate that AP asymmetry can be leveraged over a specific range of channel lengths to enhance neural recordings and enable a simple yet advantageous means for discrimination between efferent and afferent neural activity occurring simultaneously in mixed nerves. Specific guidelines for optimal electrode placement have been investigated and provided, and were based on computer simulations of "real" AP waveforms (i.e., M&L and P&B waveform) and idealized linear versions of these. Analytical expressions were derived and presented for computing the maximum amplitude of the $2^{nd}$ Difference term as a function of AP characteristics (i.e., temporal properties, amplitude, and speed) and electrode placement and channel length.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Brindley, G. (1977). An implant to empty the bladder or close the urethra. *Journal of Neurology, Neurosurgery & Psychiatry*, 40(4), 358-369.

Chew, D. J., Zhu, L., Delivopoulos, E., Minev, I. R., Musick, K. M., Mosse, C. A., . . . McMahon, S. B. (2013). A microchannel neuroprosthesis for bladder control after spinal cord injury in rat. *Science translational medicine*, 5(210), 210ra155-210ra155.

FitzGerald, J. J., Lacour, S. P., McMahon, S. B., & Fawcett, J. W. (2008). Microchannels as axonal amplifiers. *IEEE transactions on biomedical engineering*, 55(3), 1136-1146.

Hoffer, J. A., & Kallesoe, K. (2001). How to use nerve cuffs to stimulate, record, or modulate neural activity. *Neural Prostheses for Restoration of Sensory and Motor Function*, 139-178.

Marks, W. B., & Loeb, G. E. (1976). Action currents, internodal potentials, and extracellular records of myelinated mammalian nerve fibers derived from node potentials. *Biophysical journal*, 16(6), 655-668.

Meier, J. H., Rutten, W. L., & Boom, H. B. (1998). Extracellular potentials from active myelinated fibers inside insulated and noninsulated peripheral nerve. *IEEE transactions on biomedical engineering*, 45(9), 1146-1153.

Paintal, A. (1966). The influence of diameter of medullated nerve fibres of cats on the rising and falling phases of the spike and its recovery. *The Journal of physiology*, 184(4), 791-811.

Pearson, K., Stein, R., & Malhotra, S. (1970). Properties of action potentials from insect motor nerve fibres. *Journal of Experimental Biology*, 53(2), 299-316.

Plonsey, R., & Barr, R. C. (2007). *Bioelectricity: a quantitative approach*: Springer Science & Business Media.

Stein, R., Gordon, T., Hoffer, J., Davis, L., & Charles, D. (1980). Long-term recordings from cat peripheral nerves during degeneration and regeneration: implications for human nerve repair and prosthetics. *Nerve Repair: Its Clinical and Experimental Basis*, 166-176.

Stein, R., & Pearson, K. (1971). Predicted amplitude and form of action potentials recorded from unmyelinated nerve fibres. *Journal of theoretical biology*, 32(3), 539-558.

Stein, R. B., Charles, D., Davis, L., Jhamandas, J., Mannard, A., & Nichols, T. (1975). Principles underlying new methods for chronic neural recording. *Canadian Journal of Neurological Sciences/Journal Canadien des Sciences Neurologiques*, 2(03), 235-244.

Stein, R. B., Nichols, T., Jhamandas, J., Davis, L., & Charles, D. (1977). Stable long-term recordings from cat peripheral nerves. *Brain research*, 128(1), 21-38.

Struijk, J. J. (1997). The extracellular potential of a myelinated nerve fiber in an unbounded medium and in nerve cuff models. *Biophysical journal*, 72(6), 2457.

Struijk, J. J., & Thomsen, M. (1995). *Tripolar nerve cuff recording: stimulus artifact, EMG and the recorded nerve signal*. Paper presented at the Engineering in Medicine and Biology Society, 1995., IEEE 17th Annual Conference.

Struijk, J. J., Thomsen, M., Larsen, J. O., & Sinkjær, T. (1999). Cuff electrodes for long-term recording of natural sensory information. *IEEE engineering in medicine and biology magazine*, 18(3), 91-98.

What is claimed is:

1. A device for recording neural activity, the device comprising:
   a first cylindrical substrate to be positioned on a nerve and comprising a channel formed therewithin;
   a first recording electrode disposed within the channel, and in direct physical contact with the first cylindrical substrate, for recording neural activity of the nerve:
   a second cylindrical substrate disposed around, and physically separated from, the first cylindrical substrate: and
   a first reference electrode disposed between the first cylindrical substrate and the second cylindrical substrate, in direct physical contact with the second cylindrical substrate, and in electrical contact with the first recording electrode,
   the first recording electrode being positioned in an offset position with respect to a length of the channel.

2. The device according to claim 1, the first recording electrode being positioned closer to one end of the channel than to a center point of the channel with respect to the length of the channel.

3. The device according to claim 1, the length of the channel being greater than 12.8 mm.

4. The device according to claim 1, the first recording electrode being positioned a first distance from an end of the channel, the first distance being 2.1 mm or 6.4 mm.

5. The device according to claim 1, further comprising a second recording electrode disposed within the channel, and in direct physical contact with the first cylindrical substrate, for recording neural activity of the nerve, the second recording electrode being positioned in an offset position with respect to the length of the channel.

6. The device according to claim 5, the channel comprising a first end and a second end, the first recording electrode being positioned closer to the first end of the channel than to the second end of the channel, and the second recording electrode being positioned closer to the second end of the channel than to the first end of the channel.

7. The device according to claim 5, the second recording electrode being positioned closer to one end of the channel than to a center point of the channel with respect to the length of the channel.

8. The device according to claim 5, the second recording electrode being positioned a second distance from an end of the channel, the second distance being 2.1 mm or 6.4 mm.

9. The device according to claim 5, the channel comprising a first end and a second end, the first recording electrode being positioned a first distance from the first end of the channel, the first distance being 2.1 mm or 6.4 mm, and the second recording electrode being positioned a second distance from the second end of the channel, the second distance being equal to the first distance.

10. The device according to claim 5, the first recording electrode comprising at least one of silver, gold, platinum, and iridium, and the second recording electrode comprising at least one of silver, gold, platinum, and iridium.

11. The device according to claim 5, further comprising:
    a bonding bridge disposed between the first cylindrical substrate and the second cylindrical substrate, and in direct physical contact with the first cylindrical substrate and the second cylindrical substrate, for bonding the first cylindrical substrate and the second cylindrical substrate: and
    a second reference electrode disposed between the first cylindrical substrate and the second cylindrical substrate, in direct physical contact with the second cylindrical substrate, and in electrical contact with the second recording electrode.

12. The device according to claim 1, the first cylindrical substrate being a flexible substrate, and the second cylindrical substrate being a flexible substrate.

13. The device according to claim 1, the first cylindrical substrate and the second cylindrical substrate each comprising at least one of silicone and polyimide.

14. The device according to claim 1, the first cylindrical substrate being a cuff.

15. The device according to claim 1, the channel formed within the first cylindrical substrate being a microchannel.

16. A method of recording neural activity of a nerve, the method comprising:
    providing a recording device, the device comprising:
      a first cylindrical substrate to be positioned on a nerve and comprising a channel formed therewithin; and
      a first recording electrode disposed within the channel, and in direct physical contact with the first cylindrical substrate, for recording neural activity of the nerve;

a second cylindrical substrate disposed around, and physically separated from, the first cylindrical substrate; and a first reference electrode disposed between the first cylindrical substrate and the second cylindrical substrate, in direct physical contact with the second cylindrical substrate, and in electrical contact with the first recording electrode, the first recording electrode being positioned in an offset position with respect to a length of the channel;

placing the recording device around the nerve; and recording the neural activity from the nerve using the recording device.

17. The method according to claim 16, the recording of the neural activity comprising using the first recording electrode to record at least one characteristic of a first AP from the nerve.

18. The method according to claim 17, the device further comprising a second recording electrode disposed within the channel, and in direct physical contact with the first cylindrical substrate, for recording neural activity of the nerve, the channel comprising a first end and a second end, the first recording electrode being positioned closer to the first end of the channel than to the second end of the channel, the second recording electrode being positioned closer to the second end of the channel than to the first end of the channel, and the recording of the neural activity further comprising using the second recording electrode to record at least one characteristic of a second AP from the nerve, the second AP being different from the first AP.

19. The method according to claim 18, the nerve being a mixed nerve, and the method further comprising using the first recording electrode and the second recording electrode to distinguish afferent APs of the mixed nerve from efferent APs of the mixed nerve based on a comparison of an amplitude of an AP recorded by each.

20. A device for recording neural activity, the device comprising:

a first cylindrical substrate to be positioned on a nerve and comprising a channel formed therewithin; and a first recording electrode disposed within the channel, and in direct physical contact with the first cylindrical substrate, for recording neural activity of the nerve;

a second recording electrode disposed within the channel, and in direct physical contact with the first cylindrical substrate, for recording neural activity of the nerve;

a second cylindrical substrate disposed around, and physically separated from, the first cylindrical substrate;

a first reference electrode disposed between the first cylindrical substrate and the second cylindrical substrate, in direct physical contact with the second cylindrical substrate, and in electrical contact with the first recording electrode, electrode;

a second reference electrode disposed between the first cylindrical substrate and the second cylindrical substrate, in direct physical contact with the second cylindrical substrate, and in electrical contact with the second recording electrode; and a bonding bridge disposed between the first cylindrical substrate and the second cylindrical substrate, and in direct physical contact with the first cylindrical substrate and the second cylindrical substrate, for bonding the first cylindrical substrate and the second cylindrical substrate, the first recording electrode being positioned in an offset position with respect to a length of the channel, the second recording electrode being positioned in an offset position with respect to the length of the channel, the channel comprising a first end and a second end, the length of the channel being greater than 12.8 mm, the first recording electrode being positioned a first distance from the first end of the channel, the first distance being 2.1 mm or 6.4 mm, the second recording electrode being positioned a second distance from the second end of the channel, the second distance being equal to the first distance, the first recording electrode comprising at least one of silver, gold, platinum, and iridium, the second recording electrode comprising at least one of silver, gold, platinum, and iridium, the first cylindrical substrate being a flexible substrate, the second cylindrical substrate being a flexible substrate, the first cylindrical substrate being a cuff, and the channel formed within the first cylindrical substrate being a microchannel.

* * * * *